US012729237B2

(12) United States Patent
Rubsamen et al.

(10) Patent No.: US 12,729,237 B2
(45) Date of Patent: Sep. 8, 2026

(54) CONTROLLED RELEASE OF ANTIBODIES TO MODULATE CYTOKINES

(71) Applicant: Flow Pharma, Inc., Redwood City, CA (US)

(72) Inventors: Reid M. Rubsamen, Alamno, CA (US); Scott Burkholtz, Redwood City, CA (US); Charles V. Herst, Oakland, CA (US); Tom Hodge, Redwood City, CA (US); Lu Wang, San Jose, CA (US)

(73) Assignee: Flow Pharma, Inc., Redwood City, CA (US)

( * ) Notice: Subject to any disclaimer, the term of this patent is extended or adjusted under 35 U.S.C. 154(b) by 434 days.

(21) Appl. No.: 17/202,770

(22) Filed: Mar. 16, 2021

(65) Prior Publication Data

US 2021/0292406 A1 Sep. 23, 2021

Related U.S. Application Data

(60) Provisional application No. 63/041,617, filed on Jun. 19, 2020, provisional application No. 62/992,136, filed on Mar. 19, 2020, provisional application No. 62/991,456, filed on Mar. 18, 2020.

(51) Int. Cl.

| | |
|---|---|
| ***C07K 16/24*** | (2006.01) |
| ***A61K 9/00*** | (2006.01) |
| ***A61K 39/00*** | (2006.01) |
| ***A61K 47/68*** | (2017.01) |
| ***C07K 16/28*** | (2006.01) |
| ***G01N 33/68*** | (2006.01) |
| *A61K 9/16* | (2006.01) |

(52) U.S. Cl.

CPC ........ *C07K 16/248* (2013.01); *A61K 47/6883* (2017.08); *C07K 16/2866* (2013.01); *G01N 33/6869* (2013.01); *G01N 2333/5412* (2013.01)

(58) Field of Classification Search

CPC .............. C07K 16/248; C07K 16/2866; A61K 47/6883; G01N 33/6869; G01N 2333/5412

See application file for complete search history.

(56) References Cited

U.S. PATENT DOCUMENTS

| | | | | |
|---|---|---|---|---|
| 2007/0099855 A1 | | 5/2007 | Cinatl | |
| 2014/0193510 A1 | | 7/2014 | Eliasof et al. | |
| 2015/0297821 A1 | * | 10/2015 | Rae | B01J 47/02 210/322 |
| 2016/0038596 A1 | * | 2/2016 | Wright | A61M 5/315 604/72 |
| 2016/0184330 A1 | * | 6/2016 | Sordillo | A61K 9/0019 506/9 |

FOREIGN PATENT DOCUMENTS

| | | | | |
|---|---|---|---|---|
| WO | WO 2017/222935 A1 | | 12/2017 | |
| WO | WO-2019126783 A1 | * | 6/2019 | A61K 31/4535 |
| WO | WO-2019191030 A1 | * | 10/2019 | A61K 31/47 |
| WO | WO-2019217780 A1 | * | 11/2019 | A61K 31/337 |
| WO | WO-2020023335 A1 | * | 1/2020 | A61K 38/1793 |

OTHER PUBLICATIONS

Liu et al. The potential role of IL-6 in monitoring severe case of coronavirus disease 2019. Pre-Print Posted on medRxiv: Mar. 10, 2020 (Year: 2020).*

Ronco et al. Coronavirus Epidemic and Extracorporeal Therapies in Intensive Care: si vis pacem para bellum. Blood Purification. 49(3): 255-258; Published: Mar. 13, 2020 (Year: 2020).*

Chen et al. Measuring IL-6 and sIL-6R in serum from patients treated with tocilizumab and/or siltuximab following CAR T cell therapy. (Journal of Immunological Methods. 434: 1-8; Published: Apr. 3, 2016 (Year: 2016).*

Wendy Covert. Best Practices: An Update on CAR-T cells and CRS Management with Cellular Therapy: The Rocky Road to Remission. 2018 BMT Pharmacists Conference; Presented: Feb. 24, 2018. https://bmt.confex.com/tandem/2018/meetingapp.cgi/Session/3832 (Year: 2018).*

Neelapu et al. Chimeric antigen receptor T-cell therapy—assessment and management of toxicities. Nature Reviews Clinical Oncology. 15: 47-62; Published: Sep. 19, 2017 (Year: 2017).*

Le et al. FDA Approval Summary: Tocilizumab for Treatment of Chimeric Antigen Receptor T Cell-Induced Severe or Life-Threatening Cytokine Release Syndrome. Oncologist. 23 (8): 943-947; Published: Apr. 5, 2018 (Year: 2018).*

Abdallah et al. Pharmacokinetic and Pharmacodynamic Analysis of Subcutaneous Tocilizumab in Patients With Rheumatoid Arthritis From 2 Randomized, Controlled Trials. Journal of Clinical Pharmacology. 57 (4): 459-468; Published: Nov. 17, 2016 (Year: 2016).*

Prescribing Information for Sylvant (siltuximab; anti-IL-6 antibody); revised: Dec. 2019 (Year: 2019).*

Actemra (tocilizumab; anti-IL-6R antibody) Prescribing Information; Published: Jun. 2019 (Year: 2019).*

Diagnosis and Treatment Protocol for COVID-19 (Trial Version 7). National Health Commission of the People's Republic of China. Published: Mar. 3, 2020 (Year: 2020).*

(Continued)

*Primary Examiner* — Juliet C Switzer
*Assistant Examiner* — Katherine Ann Holtzman
(74) *Attorney, Agent, or Firm* — King & Spalding

(57) ABSTRACT

An injectable formulation, comprising: poly(lactic-co-glycolic (PLGA) microsphere encapsulating siltuximab, wherein microspheres are sized to release siltuximab over a period of hours, days and weeks, where the biocompatible polymer releases antibody at an absorption rate which is characterized by an absorption rate constant (Ka ($h^{-1}$) in the range of (0.001 to 2.048)+/−20%, or +/−10%, or +/−5% . . . for use and treating human patients with infections. The invention includes treating patients with viral infections of SARS-Cov-2 using siltuximab.

8 Claims, 24 Drawing Sheets

(56) References Cited

OTHER PUBLICATIONS

Senchenkova et al. Novel Role of T Cells and IL-6 (Interleukin-6) in Angiotensin II-Induced Microvascular Dysfunction Hypertension. 73:829-838; Published: Apr. 2019 (Year: 2019).*
Velazquez-Salinas et al. The Role of Interleukin 6 During Viral Infections. Frontiers in Microbiology. 10: 1067; Published: May 10, 2019 (Year: 2019).*
Velasquez et al. Clinical Infectious Diseases. 61(7): 1135-1140; Published: Jun. 30, 2015 (Year: 2015).*
Glynn et al. Lancet Infectious Diseases. 17(6): 645-653; Published: Jun. 2017 (Year: 2017).*
Banadyga et al. Open Forum Infectious Diseases. 6(3): ofz046; Published: Mar. 2019 (Year: 2019).*
Hutchinson et al. The Journal of Infectious Diseases. 196(Supplement 2): S357-S363; Published: Nov. 15, 2007 (Year: 2007).*
Baize et al. Clinical and Experimental Immunology. 128: 163-168; Published: Apr. 2002 (Year: 2002).*
McElroy et al. The Journal of Infectious Diseases. 210: 558-566; Published: Feb. 12, 2014 (Year: 2014).*
Vernet et al. JCI Insight. 2(6): e88864; Published: Mar. 23, 2017 (Year: 2017).*
Wauquier et al. PLoS Neglected Tropical Diseases. 4(10): e837; Published: Oct. 5, 2010 (Year: 2010).*
Broadhurst et al. Clinical Microbiology Reviews. 29(4): 773-793; Published: Oct. 2016 (Year: 2016).*
Salama et al., "Tocilizumab in Patients Hospitalized with Covid-19 Pneumonia." The New England Journal of Medicine, Apr. 22, 2021, 384;1503-1516, pp. 20-30.
The REMAP-CAP Investigators "Interleukin-6 Receptor Antagonists in Critically Ill Patients with COVID-19." American College of Cardiology, Mar. 5, 2021, pp. 1-5.
Ronco et al. "Coronavirus Epidemic and Extracorporeal Therapies in Intensive Care: si vis pacem para bellum," Blood Purification, Mar. 13, 2020 (Mar. 13, 2020), vol. 49, Iss. 3, pp. 255-258, entire document.
Cui et al., "Monoclonal antibodies: formulations of marketed products and recent advances in novel delivery system," Drug Development and Industrial Pharmacy England, Informa Healthcare, US, vol. 43, No. 4, 2017, pp. 519-530, XP009194748.
Solhjou et al., "Novel Application of Localized nanodelivery of anti-interleukin-6 protects organ transplant from ischemia-reperfusion injuries," American Journal of Transplantation Blackwell Munksgaard, vol. 17, No. 9, 2017, pp. 2326-2337, XP072343498.
Lima et al., "Neutralization of pro-inflammatory cytokines by intra-articular injection of biofunctionalized nanoparticles as an advanced treatment for osteoarthritis" 2019, pp. 1-1, XP093128903, Retrieved from the Internet: URL: https://api.3bs.uminho.pt/sites/default/files/biblio/19975-poster_ana_lima.pdf.>.
Mehta et al., "COVID-19: consider cytokine storm syndromes and immunosuppression," The Lancet, Elsevier, Amsterdam, NL, vol. 395, No. 10229, 2020, XP086105444.
"Eusa pharma and the papa giovanni XXIII hospital, bergamo, italy announce initiation of an observational case-control study of siltuximab in patients with COVID-19 who have developed serious respiratory complications: business wire," 2020, pp. 1-4, XP093129569, Retrieved from the Internet: URL: https://www.businesswire.com/news/home/20200318005218/en/.
John B. Moore et al: "Cytokine release syndrome in severe COVID-19", Science, vol. 368, No. 6490, May 1, 2020 (May 1, 2020), pp. 473-474, XP055741759, US ISSN: 0036-8075, DOI: 10.1126/science.abb8925.
Liu Bingwen et al: "Can we use interleukin-6 (IL-6) blockade for coronavirus disease 2019 (COVID-19)-induced cytokine release syndrome (CRS)?", Journal of Autoimmunity, vol. 111, Jul. 1, 2020 (Jul. 1, 2020), p. 102452, XP093179789, GB ISSN: 0896-8411, DOI: 10.1016/j.jaut.2020.102452.
Sinha Pranay et al: "Early administration of interleukin-6 inhibitors for patients with severe COVID-19 disease is associated with decreased intubation, reduced mortality, and increased discharge", International Journal of Infectious Diseases, International Society for Infectious Diseases, Hamilton, CA, vol. 99, Jul. 25, 2020 (Jul. 25, 2020), pp. 28-33, XP086298593, ISSN: 1201-9712, DOI: 10.1016/J.IJID.2020.07.023.
Mckee Selina: "Positive early data from siltuximab COVID-19 trial—PharmaTimes", Apr. 2, 2020 (Apr. 2, 2020), pp. 1-7, XP093179795.
Gritti Giuseppe et al: "IL-6 signalling pathway inactivation with siltuximab in patients with COVID-19 respiratory failure: an observational cohort study", medRxiv, Apr. 3, 2020 (Apr. 3, 2020), pp. 1-17, XP093179796, DOI: 10.1101/2020.04.01.20048561.
Anonymous: "Interpretation of the "Diagnosis and Treatment Plan for Novel Coronavirus Pneumonia (Trial Version 7)" translation by google translate", Mar. 4, 2020 (Mar. 4, 2020), pp. 1-7, XP093180126.
Shimabukuro-Vornhagen Alexander et al: "Cytokine release syndrome", Journal for Immunotherapy of Cancer, vol. 6, No. 1, Jun. 15, 2018 (Jun. 15, 2018), XP055918827, DOI: 10.1186/s40425-018-0343-9.

* cited by examiner anti-IL-6 and anti-IL-6R 72h

Figure 4:
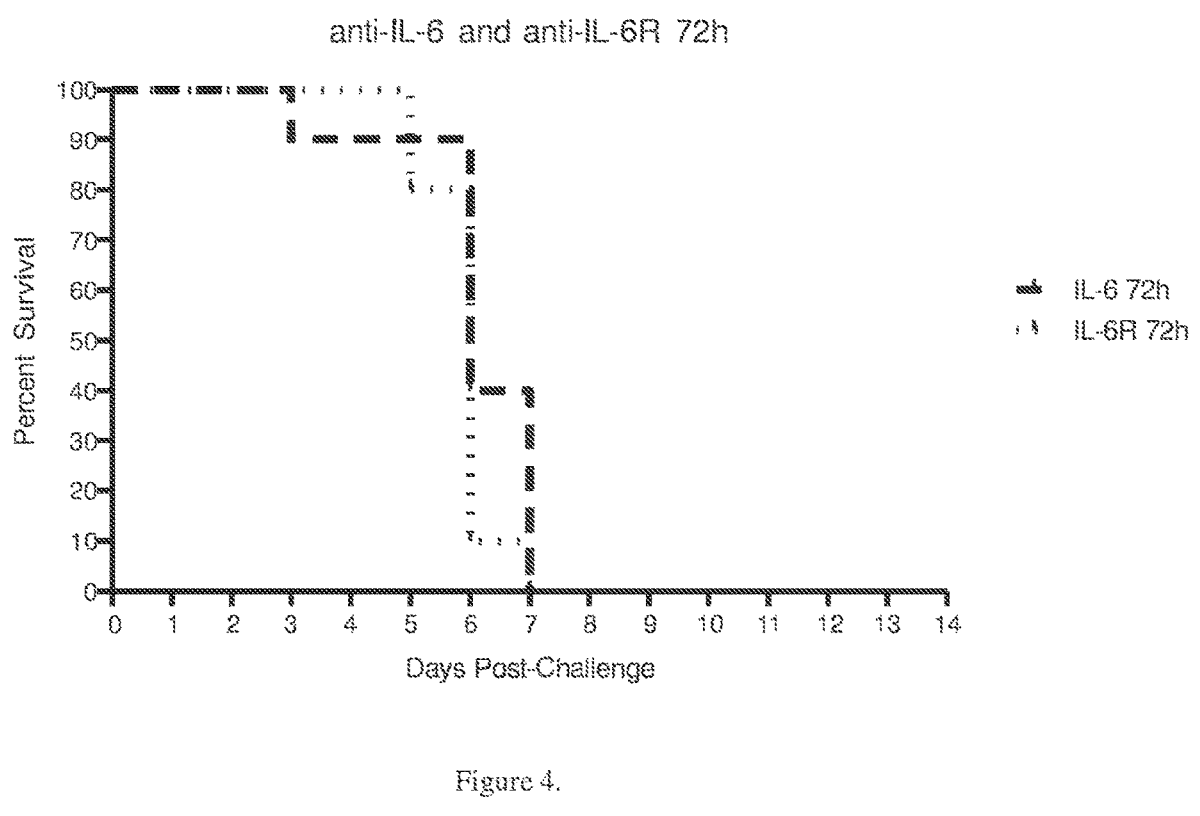

Percent Survival 100
90
80
70
60
50
40
30
20
10
0

0 1 2 3 4 5 6 7 8 9 10 11 12 13 14

Days Post-Challenge

anti-IL-6 v. anti-IL-6R 24h i.p. route Survival
(a)
Key:
anti-IL-6 - 24h Q24
anti-IL-6 - 24h Q72
anti-IL-6R - 24h Q72
Vehicle
Percent Survival
100%
90%
80%
70%
60%
50%
40%
30%
20%
10%
0%
0
1
2
3
4
5
6
7
8
9
10
11
12
13
14
15
Time (Days)

(b)
anti-IL-6 v. anti-IL-6R i.p. route 24h Clinical Observations
Average Clinical Score of Survivors
0
1
2
3
Post-Challenge Day
1
2
3
4
5
6
7
8
9
10
11
12
13
14
Legend
anti-IL-6 - 24h Q24
anti-IL-6 - 24h Q72
anti-IL-6R - 24h Q72
Vehicle (e)
anti-IL-6 v. anti-IL-6R 72h i.p. route Survival
Key:
anti-IL-6 - 72h Q72
anti-IL-6R - 72h Q72
Vehicle
Percent Survival
100%
90%
80%
70%
60%
50%
40%
30%
20%
10%
0%
Time (Days)
0
1
2
3
4
5
6
7
8
9
10
11
12
13
14
15

| Group | N | Test Article | Dosing Regimen |
|---|---|---|---|
| 1 | 6 | Dilution Buffer Vehicle (intravenous administration) | One dose 24 hours post challenge no subsequent doses given |
| 2 | 10 | anti-IL-6R mAb (100ug intravenous administration) | One dose 24 hours post challenge no subsequent doses given |
| 3 | 10 | | One dose 48 hours post challenge no subsequent doses given |
| 4 | 10 | | One dose 72 hours post challenge no subsequent doses given |

Figure 17.

| Antibody | Route | Dose (ug) | Dose (mg/Kg) | $T_{1/2}$(h) | $K_e$($h^{-1}$) | $K_a$($h^{-1}$) | $V_d$(L/Kg) | F |
|---|---|---|---|---|---|---|---|---|
| anti-IL-6R | IV | 100 | 5 | 223 | 0.0031 | - | 0.05 | 1 |
| anti-IL-6R | IP | 400 | 20 | 223 | 0.0031 | 0.5 | 0.05 | 0.5 |
| anti-IL-6 | IP | 400 | 20 | 57 | 0.0122 | 0.5 | 0.05 | 0.5 |

Figure 18.

| Clinical Score | Description of Animal |
|---|---|
| 1 | Healthy |
| 2 | Lethargic and/or ruffled fur (triggers a second observation) |
| 3 | Ruffled fur, lethargic and hunched posture, orbital tightening (triggers a third observation) |
| 4 | Ruffled fur, lethargic, hunched posture, orbital tightening reluctance to move when stimulated, paralysis or greater than 20% weightloss (requires immediate euthanasia) |
| (no score) | Deceased |

Figure 19.

CONTROLLED RELEASE OF ANTIBODIES TO MODULATE CYTOKINES

FIELD OF THE INVENTION

The invention relates generally to injectable controlled release formulations useful in the treatment of infections in human patients. More specifically, the invention relates to injectable formulations comprising a range of particles of different sizes comprised of a biocompatible polymer surrounding antibodies or antigenic binding fractions of such antibodies which bind to and block the effects of cytokines such as IL-6 cytokines.

BACKGROUND OF THE INVENTION

Under normal circumstances, interleukin-6 (IL-6) is secreted transiently in response to injury or infections. However, unregulated synthesis and secretion of IL-6 has contributed to a host of pathological effects such as rheumatoid arthritis. (Swaak et al., 1988) Furthermore, IL-6 induces differentiation of B cells and naïve CD4+ T cells and inhibits TGF-beta differentiation, providing a crucial link between innate and acquired immune responses. (Korn et al., 2008; Takamatsu et al., 2018; Dienz and Rincon, 2009) These actions place IL-6 in a central role in mediating and amplifying cytokine release syndrome, commonly associated with Ebola and SARS-COV-2 infections. (Conti et al., 2020)

Patients with COVID-19, the disease caused by infection with SARS-COV-2, can present with debilitating pneumonia and other complications including acute respiratory distress syndrome (ARDS) (Zhou et al., 2020; Chen et al., 2020; Huang et al., 2020a; Lescure et al., 2020).

Elevated IL-6 was found to be significantly correlated with death in COVID-19 patients (Ruan et al., 2020). Originally developed for the treatment of arthritis, anti-IL-6R mAbs have been used to treat CRS as a complication of cancer therapy using adaptive T-cell therapies. (Tanaka et al., 2016; Ascierto et al., 2020; Lee et al., 2014).

Warnings admonishing use of IL-6 blockers in the context of acute infection are present in the package inserts for tocilizumab (Genentech, 2014), sarilumab (Sanofi, 2017) and siltuximab (EUSA, 2015). However, the potential value of using these biologics to treat COVID-19 patients was discussed early during the SARS-COV-2 outbreak (Mehta et al., 2020a; Liu et al., 2020). Ebola virus infection is well known to produce CRS, and IL-6 serum levels are known to be inversely correlated with survival in patients post-infection (Wauquier et al., 2010).

Recent evidence suggests that patients with clinically severe SARS-COV-2 infection might also have a CRS syndrome (Huang et al., 2020b). Similarly, the severity of SARS-CoV-1 infection has been shown to be associated with increased serum concentrations of IL-6, leading clinical scientists to propose non-corticosteroid based immunosuppression by using IL-6 blockade as a means to treat hyper inflammation observed in certain patients with SARS-COV-2 infections (Mehta et al., 2020b; Wong et al., 2004). Indeed, a recent (5/24/2020) search of ClinicalTrials.gov revealed at least 62 clinical trials examining the efficacy and safety of anti-IL-6R monoclonal antibodies (mAbs) and anti-IL-6 mAb for management of patients with COVID-19 (45 studies for tocilizumab (anti-IL-6R mAb), 14 for sarilumab (anti-IL-6R mAb) and 3 for siltuximab (anti-IL-6 mAb)). Early mixed results of CRS treatment with IL-6 blockers (Herper, 2020; Cli, 2020; Taylor, 2020; Saha et al., 2020), and observations of the role of IL-6 in morbidity and mortality associated with Ebola virus infection (Herst et al., 2020), led us to evaluate the clinical effects of treatment with not only antibody directed against the IL-6 receptor (anti-IL-6R mAb), but also with mAb directed to IL-6 itself (anti-IL-6 mAb).

There are observed differences between treatments with anti-IL-6R and anti-IL-6 mAbs. Thus, IL-6 blockade provides a therapy for patients with Ebola infection as well as patients infected with SARS-COV-2.

COVID-19 is caused by the SARS-COV-2 virus and produces a potentially lethal situation in which patients rapidly succumb to multiple organ failure, typically heralded by pneumonia.

The progression of the disease is first insidious and then rapid, making early diagnosis and treatment difficult. There are currently no approved vaccines or antiviral therapies for COVID-19. The disease is particularly severe in the elderly and in patients with co-existing medical conditions.

Patients with high blood pressure, for example, even if it is adequately treated, can have over expression of the ACE2 protein on cardiac and other tissues. This is critical because the SARS-COV-2 virus enters cells in part facilitated by the presence of the ACE2 protein in the cell membrane. This, ironically, produces a situation where environments in which patients are aggressively treated for hypertension using, for instance alpha receptor blockers are actually at a higher risk of dying from COVID-19.

The world is currently working diligently to develop vaccines and anti-viral therapies directed against SARS-COV-2.

The relatively short period of time between presentation with symptoms and death, especially in the elderly is extremely concerning. Patients presenting for emergent evaluation of respiratory symptoms have in some cases required mechanical ventilation for respiratory failure within 12 or 24 hours after initial onset of relatively mild symptoms. This makes the search for therapies that could blunt the progression of disease especially important, even if these therapies themselves are not definitive.

It is known that one of the mechanisms by which COVID-19 causes respiratory failure and subsequent multi-organ failure requiring mechanical ventilation and management of the patient in the ICU is a phenomenon called cytokine storm.

This phenomenon was recognized in the context of other viral diseases such as Ebola and occurs when cytokines, which include interleukins, such as Interleukin-6 (IL-6), are released as part of the immune system's response to viral infection.

These cytokines can facilitate innate immunity, providing some protection against the viral infection in a patient who does not have an antibody response yet developed to that virus.

Unfortunately, in addition to augmenting innate immunity, these cytokines can cause lung damage and a picture of septic shock producing respiratory failure, hypotension and multi-organ failure, in some cases very quickly.

Because of the known relationship of SARS-COV-2 to infection and cytokine release and the serious clinical consequences of this relationship, especially in the elderly, researchers have looked at ways to block the effect of specific cytokines in the context of SARS-COV-2 infection.

The search for ways to manage cytokine storm has led to multiple clinical trials of IL-6 inhibitors. There are multiple IL-6 inhibitors available both as approved products for other indications, as well as products in the pharmaceutical development pipeline. Two approved products are Actemra® (tocilizumab, Roche/Chugai) and Kevzara®(sarilumab, Sanofi/Regeneron/Asahi Kasei) that are designed to block the IL-6 receptor (IL-6R) as a mechanism for treating inflammatory disease. In this case, arthritis.

Anti IL-6R antibodies have been successfully used to treat cytokine storm in the context of chemotherapy using CAR-T therapy for patients with B-cell leukemia or lymphoma.

There are at least eleven other anti-IL-6, six receptor blocking agents in development for various clinical applications around the world.

Researchers favor blocking receptors where possible because receptor blockade does not require a knowledge of how much receptor agonist is present in order to provide the desired clinical effect.

However, there is also a direct anti-IL-6 antibody available, which has been approved for a rare condition known as Castleman's disease (SYLVANT® (siltuximab), EUSA).

SUMMARY OF THE INVENTION

Certain types of infections and in particular certain types of viral infections elicit a range of different responses including the release of large amounts of cytokines. Cytokines are part of the innate immune response, which consists of physical, chemical and cellular defenses against pathogens such as viruses. As such, an appropriate level, cytokines are useful in fighting the infection. However, when the level is undesirably high in concentration it is said to result in a "cytokine storm" which produces organ injury, and in particular, lung injury which can lead to Adult Respiratory Distress Syndrome (ARDS) requiring intensive care therapy, endotracheal intubation, extracorporeal oxygenation (ECMO) and can lead to death. In order to obtain the benefits of cytokines and not the adverse effects of a cytokine storm, the present invention provides for an injectable formulation comprised of particles which encapsulate antibodies which bind to the cytokines. The formulation preferably includes a small amount of free antibody not associated with any biocompatible polymer which encapsulates the antibodies. The free antibodies provide for initial action or immediate impact on modulating down any potential beginnings of a cytokine storm. However, free antibody is present in a relatively small amount so as to not eliminate the positive effects of the cytokines in defeating the infection. Additional release of antibody is made available in a second phase when the biocompatible polymer of a first group of particles is dissolved there by releasing antibody. This can be repeated a plurality of times to provide release of antibody in a third fourth, fifth etc. phase when the biocompatible polymer of second, third, fourth, etc. groups of particles are dissolved there by releasing antibody in a plurality of phases.

An aspect of the invention is a method of treatment, comprising:

- diagnosing a patient with an infection associated with a cytokine storm;
- administering to the patient a therapeutically effective amount of an injectable formulation comprising a pharmaceutically acceptable carrier, free anti-IL-6 antibody, and a first group anti-IL-6 antibodies encapsulated in particles of a biocompatible polymer; and allowing the free anti-IL-6 antibodies to bind IL-6 cytokines in the patient and provide for an initial phase of modulating down of cytokine effects in the patient, and allowing first group anti-IL-6 antibodies encapsulated in particles to dissolve and thereafter the antibodies to bind IL-6 cytokines in the patient and provide for a second phase of modulating down of cytokine effects in the patient.

The invention shows direct neutralization of IL-6 with an a-IL-6 mAb in a BALB/c Ebolavirus (EBOV) challenge model producing a statistically significant improvement in outcome compared with controls when administered within the first 24 h of challenge and repeated every 72 h. A similar effect was seen in mice treated with the same dose of a-IL-6R mAb when the treatment was delayed 48 h post-challenge. This shows that direct neutralization of IL-6, early during the course of infection, provides additional clinical benefits to IL-6 receptor blockade alone during treatment of patients with virus-induced CRS.

An aspect of the invention is a use of an injectable formulation, comprising:

- diagnosing a patient with an infection known to be capable of producing cytokine release syndrome;
- administering to the patient by a type of injection selected from the group consisting of subcutaneous and intramuscular, a therapeutically effective amount of an injectable formulation comprising a pharmaceutically acceptable carrier, free anti-IL-6 antibody, and a first group of anti-IL-6 antibodies encapsulated in particles of a biocompatible polymer; and
- allowing the free anti-IL-6 antibodies to bind IL-6 cytokines in the patient and provide for an initial phase of modulating down of cytokine effects in the patient, and
- allowing the first group of anti-IL-6 antibodies encapsulated in particles to dissolve and thereafter the antibodies to bind IL-6 cytokines in the patient and provide for a second phase of modulating down of cytokine effects in the patient.

The use described above includes, wherein the injectable formulation further comprises:

- a second group of anti-IL-6 antibodies encapsulated in particles of a biocompatible polymer whereby the particles of the second group begin to dissolve after the particles of the first group.

The use described above includes, wherein the injectable formulation further comprises:

- a third group anti-IL-6 antibodies encapsulated in particles of a biocompatible polymer whereby the particles of the third group begin to dissolve after the particles of the second group.

The use described above includes, wherein the injectable formulation further comprises:

- a plurality of groups of particles of anti-IL-6 antibodies encapsulated in a biocompatible polymer whereby the particles of different groups of the plurality of groups dissolve at different rates relative to other groups thereby providing for controlled release of the antibody and controlled modulation of cytokines.

The use described above includes, wherein the antibody is siltuximab, and the patient is diagnosed by chest imaging.

An aspect of the invention is injectable formulation, comprising:

- a poly(lactic-co-glycolic (PLGA) microsphere encapsulating siltuximab.

The formulation may further comprise:

- an injectable carrier and wherein microspheres are sized to release siltuximab over a period selected from the group consisting of hours, days and weeks.

The formulation may allow the biocompatible polymer to releases antibody at an absorption rate which is characterized by an absorption rate constant (Ka (h−1) selected from the group consisting of (0.001, 0.002, 0.004, 0.008, 0.016, 0.032, 0.064, 0.128. 0.256, 0.512, 1.024, 2.048)+/−20%, or +/−10%, or +/−5% . . . .

An aspect of the invention is an injectable formulation, comprising:

diagnosing a patient with an infection of SARS-COV-2 virus;

administering to the patient by a type of injection selected from the group consisting of subcutaneous and intramuscular injection a therapeutically effective amount of an injectable formulation of a siltuximab anti-IL-6 antibody encapsulated in a biocompatible polymer; and allowing the anti-IL-6 antibody to bind IL-6 cytokines.

The use described above includes, wherein, wherein the diagnosing is carried out by a method selected from the group consisting of Reverse Transcriptase Polymerase Chain Reaction (RT-PCR) and chest imaging, and wherein the biocompatible polymer is poly(lactic-co-glycolic (PLGA).

The use described above includes, wherein the formulation further comprises anti-IL-6R antibodies, and the anti-IL-6R antibodies are in a biocompatible polymer, and where the biocompatible polymer releases anti-IL-6R antibodies so as to produce an average plasma level selected from the group consisting of (250 ug/ml, 200 ug/ml, 150 ug/ml, 100 ug/ml, 50 ug/ml)+/−20%., and wherein the biocompatible polymer is poly(lactic-co-glycolic (PLGA).

The use described above includes, wherein the anti-IL6R antibody is selected from the group consisting of sarilumab and tocilizumab.

An aspect of the invention is a use of an injectable formulation, comprising:

diagnosing a patient with an infection of SARS-COV-2;

measuring a level of IL-6 in the patient to obtain an initial level;

administering to the patient by intramuscular injection a therapeutically effective amount of an injectable formulation of a therapeutically effective amount of siltuximab anti-IL-6 antibody encapsulated in a biocompatible polymer; and allowing the anti-IL-6 antibody to bind IL-6 cytokines in the patient.

The use described above may further comprise:

measuring a level of IL-6 in the patient to obtain a post treatment level;

administering to the patient by intramuscular injection an additional amount of an injectable formulation of anti-IL-6 antibody encapsulated in a biocompatible polymer wherein the amount administered is based on a differential between the initial level and the post treatment level, and repeating the measuring and administering wherein the amount administered is in each administering step is based on a differential between a prior level and a post treatment level.

An aspect of the invention is a use of an injectable formulation comprising:

diagnosing a patient with an infection associated with cytokine release syndrome;

administering to the patient at a first point in time a therapeutically effective amount of a first injectable formulation comprising a pharmaceutically acceptable carrier with free anti-IL-6 antibody, and allowing the free anti-IL-6 antibodies to bind IL-6 cytokines in the patient and provide for an initial phase of modulating down of cytokine effects in the patient, and administering to the patient at a second point in time a therapeutically effective amount of an injectable formulation comprising a pharmaceutically acceptable carrier with free anti-IL-6R antibody wherein the first point in time is separated from the second point in time by one hour or more.

An aspect of the invention is a use, wherein the formulation is administered by a type of injection selected from the group consisting of subcutaneous and intramuscular and both formulations comprise free unencapsulated antibody and antibodies encapsulated in a biocompatible polymer and where the biocompatible polymer releases anti-IL-6R antibodies so as to produce an average plasma level selected from the group consisting of (250 ug/ml, 200 ug/ml, 150 ug/ml, 100 ug/ml, 50 ug/ml)+/−5%, the method further comprising:

assaying cytokine blood levels in the patient;

re-administering at least one antibody formulation to the patient based on determined cytokine levels, and wherein the biocompatible polymer releases antibody at an absorption rate which is characterized by an absorption rate constant (Ka (h−1) selected from the group consisting of (0.001, 0.002, 0.004, 0.008, 0.016, 0.032, 0.064, 0.128. 0.256, 0.512, 1.024, 2.048)+/−5%.

An aspect of the invention is a use of an injectable formulation, comprising:

diagnosing a patient with an infection known to be associated with producing cytokine release syndrome;

administering to the patient by injection at a first point in time a therapeutically effective amount of a first injectable formulation comprising a pharmaceutically acceptable carrier, free siltuximab, and allowing the free siltuximab to bind IL-6 cytokines in the patient and provide for an initial phase of modulating down of cytokine effects in the patient, and administering to the patient at a second point in time a therapeutically effective amount of an injectable formulation comprising a pharmaceutically acceptable carrier with free anti-IL-6R antibody selected from the group consisting of sarilumab and tocilizumab, and wherein the first point in time is separated from the second point in time by one hour or more;

wherein the formulation is administered by a type of injection selected from the group consisting of subcutaneous and intramuscular and both formulations comprise free unencapsulated antibody and antibodies encapsulated in a biocompatible polymer.

The use described above may further comprise:

assaying cytokine blood levels in the patient; and re-administering at least one antibody formulation to the patient based on determined cytokine levels.

The use described above may further comprise:

wherein the biocompatible polymer releases anti-IL-6R antibodies so as to produce an average plasma level selected from the group consisting of (250 ug/ml, 200 ug/ml, 150 ug/ml, 100 ug/ml, 50 ug/ml)+/−20%.

An aspect of the invention is a use of an injectable formulation, comprising:

diagnosing a patient with an infection known to be capable of producing cytokine release syndrome;

administering to the patient by intravenous injection a therapeutically effective amount of an injectable formulation comprising a pharmaceutically acceptable carrier, and anti-IL-6 antibody wherein the formulation is injected at a rate so as to modulate down effects of cytokines and thereby avoid cytokine release syndrome.

The use described above includes, wherein the antibody is siltuximab.

The use described above may comprise:

measuring a cytokine blood level in the patient; and adjusting the rate of injection based on the measured cytokine level to allow for a normal level of cytokines, thereby avoiding cytokine release syndrome while allowing for a level of circulating cytokines.

The invention modulates down CRS thereby reducing morbidity and mortality associated with acute viral infections including those caused by filoviruses and coronaviruses In another aspect of the invention the formulation is administered by a type of injection selected from the group consisting of subcutaneous and intramuscularly.

Another aspect of the invention further comprises:

a second group anti-IL-6 antibodies encapsulated in particles of a biocompatible polymer whereby the particles of the second group begin to dissolve after the particles of the first group.

Another aspect of the invention further comprises:

a third group anti-IL-6 antibodies encapsulated in particles of a biocompatible polymer whereby the particles of the third group begin to dissolve after the particles of the second group.

Yet another aspect of the invention further comprises:

a plurality of groups of particles of anti-IL-6 antibodies encapsulated in a biocompatible polymer whereby the particles of different groups of the plurality of groups dissolve at different rates relative to other groups thereby providing for controlled release of the antibody and controlled modulation of cytokines.

In another aspect of the invention the patient is diagnosed as undergoing respiratory failure.

An aspect of the invention is a formulation useful in method of treating, comprising diagnosing a patient with a viral infection capable of producing a cytokine storm such as a viral infection with SARS-COV-2 the virus that causes COVID-19, and; administering to the patient by intramuscular or subcutaneous injection a therapeutically effective amount of an injectable formulation of anti-IL-6 antibody encapsulated in a biocompatible polymer; and allowing the anti-IL-6 antibody to bind IL-6 cytokines in the patient and thereby modulate down the cytokine storm in the patient.

In another aspect of the invention the anti-IL-6 antibody is in an injectable formulation and is administered intravenously.

In another aspect of the invention the anti-IL6 antibody is in an injectable controlled release microsphere formulation and is administered intramuscularly or subcutaneously.

In another aspect of the invention the antibody is siltuximab.

It is an object of this invention to describe the potential benefit of using antibody directed against IL-6 itself rather than antibody directed towards the IL-6 receptor (IL-6R) in order to palliate early symptoms developed during the course of SARS-COV-2 infection.

It is another object to this invention to show that the effect of anti-IL-6 antibody to clinically palliate the early onset of symptoms in the context SARS-COV-2 is superior to that of the effect of anti-IL-6R antibody in this context.

It is another object to this invention to show that anti-IL-6 antibody can be encapsulated into microspheres allowing controlled release by intramuscular or subcutaneous administration and that this administration route could facilitate mass administration of this material in an outbreak without having to start complex-to-manage, and difficult to institute, intravenous lines in patients presenting with acute COVID-19 infection.

It is another object to this invention to describe how anti-IL-6 antibody and anti-IL-6 receptor antibody could be used together to exploit the differential behavior of these antibodies in the onset of COVID-19 infection.

It is other object to this invention to describe how the potential advantage of using anti IL-6R antibody and anti-IL-6 antibody together could benefit the patient by the fact that anti IL-6 antibody may provide a superior effect early during the course of the disease and anti-IL-6R receptor antibody may provide a superior effect during the later course of the disease as it evolves rapidly during the first 14 days of the infection.

Other aspects of this invention are disclosed and described in the corresponding peer reviewed paper which is incorporated herein by reference. (Rubsamen et al., 2020)

These and other objects, advantages, and features of the invention will become apparent to those persons skilled in the art upon reading the details of the methods, steps, formulations and uses as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 4 Shows Kaplan-Meier Survival Curves after treatment with either anti-IL-6 antibody or anti-IL-6R antibody beginning 72 hours after maEBOV challenge.

FIG. 17 is a Table. I.v. delivery experiment design. All mice challenged with 100 Plaque Forming Units of maEBOV given via i.v. administration using an indwelling central venous catheter. Antibody treatments were given in a volume of 100 μL. Group 1 consisted of three male and three female mice. Groups 2-4 contained five male and five female mice in each group.

FIG. 18 is a Table. Pharmacokinetic parameters predicted based on literature values for the monoclonal antibodies used for the study are shown. T½ is the terminal half-life. Although antibody blood levels were not measured, this allowed simulated PK profiles to be created as shown in FIG. 15.

FIG. 19 is a Table. Clinical score indices used to track morbidity in study animals.

DETAILED DESCRIPTION OF THE INVENTION

Figure 1:
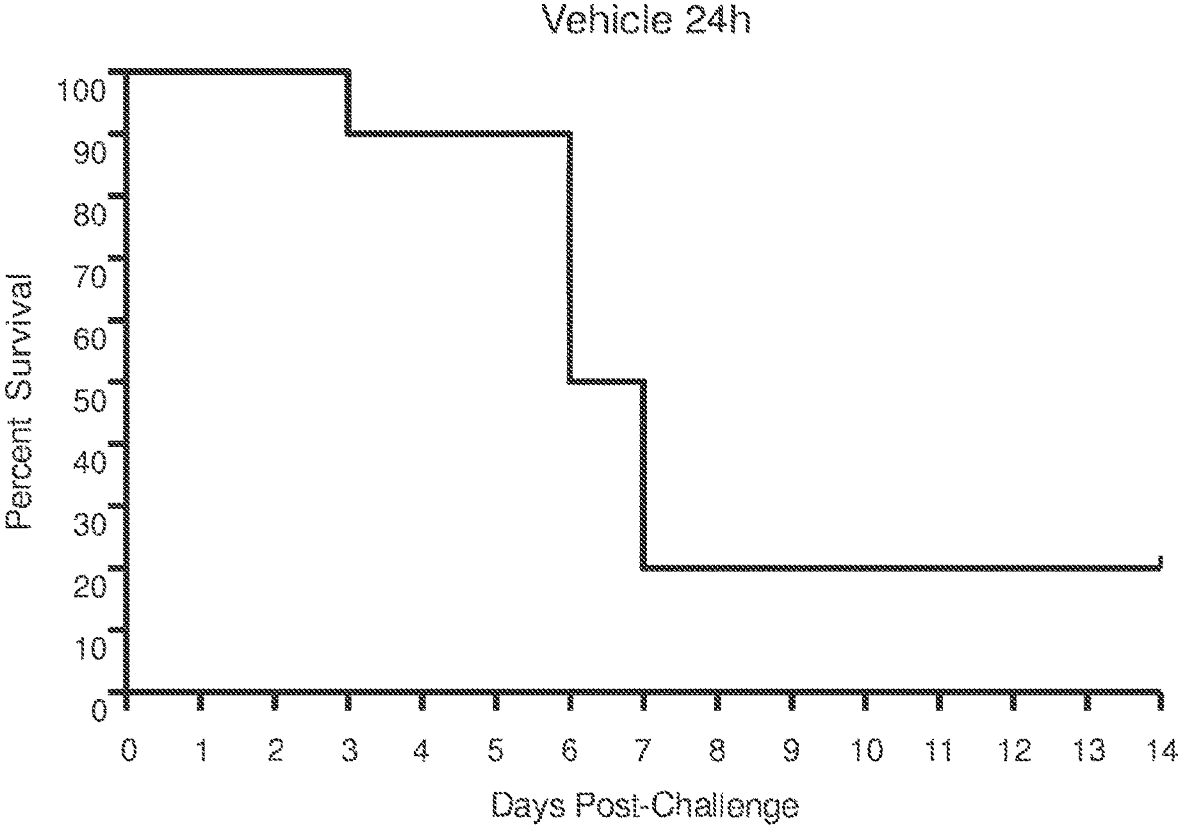
FIG. 1 is a graph showing the Kaplan-Meier Survival Curve for a pharmaceutically acceptable carrier vehicle without antibody given starting 24 hours after maEBOV challenge. The vehicle control is also given starting 24 hours after maEBOVchallenge FIG. 2 Shows Kaplan-Meier Survival Curves after treatment with either anti-IL-6 antibody or anti-IL-6R antibody beginning 24 hours after maEBOV challenge.

Before the present formulations, methods and uses are described, it is to be understood that this invention is not limited to any particular formulation, steps and/or embodiments described, as such may, of course, vary. It is also to be understood that the terminology used herein is for the purpose of describing particular formulations, steps and embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cytokine" includes a plurality of such cytokines and reference to "the diagnoses" includes reference to one or more diagnostic methods or steps and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "treatment", "treating" and the like are used herein to generally mean obtaining a desired pharmacological or physiological effect. The effect may be prophylactic in terms of completely or partially preventing a disease such as an infection or symptom thereof and may be therapeutic in terms of partially or completely curing a disease and/or adverse effect attributed to the disease or infection. "Treatment" as used herein covers any treatment of any disease and specifically modulating down a cytokine storm resulting from of harmful infectious bacterial, fungal, parasitic, and viral infections, in a mammal, particularly a human, and includes:

(a) preventing the cytokine storm from occurring or developing in the subject which may be predisposed to the infection but has not yet been diagnosed as having it;

(b) inhibiting other adverse effects of IL-6, i.e. arresting development or such adverse effects; or (c) relieving the adverse effects, i.e. causing regression of the effects. Treatment may be specifically directed towards treating patients infected with SARS-COV-2 virus.

A "cytokine storm" as used herein refers to exaggerated, excessive synthesis of IL-6 in response to any type of environmental stress including infection with a pathogen, chemical exposure and physical trauma. The term is used to refer to the result of infection known to be capable of producing cytokine release syndrome In particular the stress may be a stress induced by viral infection and more particularly viral infection caused by infection with coronavirus, COVID-19 which can produce cytokine release syndrome. The level is exaggerated or excessive when it reaches a level which is no longer beneficial. Such a level may generate a systemic inflammatory response syndrome including sepsis, macrophage activation syndrome and hemophagoccytic lymphohistiocytosis. These responses can result in total organ failure and death.

"IL-6" refers to a prototypical cytokine featuring pleiotropic and redundant functional activity. IL-6 is promptly produced mainly by macrophages in response to pathogen-associated molecular patterns (PAMPs) or damage-associated molecular patterns (DAMPs) and performs a protective function by removing infectious agents and healing damaged tissue through induction of acute phase and immune responses as well as hematopoiesis.

The mean IL-6 level in sera of healthy normal individuals is 5.9±1 μg/ml (range 5-7 μg/ml), although the Mayo Clinic sites the normal value as <1.8 μg/mL.

Siltuximab interferes with IL-6 mediated growth of B-lymphocytes and plasma cells, secretion of vascular endothelial growth factor (VEGF) and autoimmune phenomena. Administer SYLVANT 11 mg/kg over 1 hour as an intravenous infusion every 3 weeks until treatment failure. Perform hematology laboratory tests prior to each dose of SYLVANT therapy for the first 12 months and every 3 dosing cycles thereafter. Siltuximab may increase CYP450 activity leading to increased metabolism of drugs that are CYP450 substrates. Co-administration of siltuximab and CYP450 substrates with narrow therapeutic index such as warfarin, ciclosporin or theophylline should be closely monitored. Siltuximab is a chimeric monoclonal antibody that binds to interleukin-6 (IL-6), preventing binding to soluble and membrane bound interleukin-6 receptors.

Antibodies to human interleukin-6 receptor (hIL-6R) are described in U.S. Pat. Nos. 5,670,373, 5,795,965, 5,817,790, 6,410,691, 7,582,298; 9,308,256; 9,884,916; and 10,584,173 and those patents and the antibody characteristics, and sequences including their heavy chain variable region (HCVR), light chain variable region (LCVR) and Complementarity-determining region (CDR) sequences are all incorporated herein by reference.

Antibodies to human interleukin-6 (hIL-6) are described in U.S. Pat. Nos. 7,612,182; 8,178,101; 8,404,235; and 9,056,905 and those patents and the antibody characteristics, and sequences including their heavy chain variable region (HCVR), light chain variable region (LCVR) and Complementarity-determining region (CDR) sequences are all incorporated herein by reference.

Invention in General

The invention includes methods of treatment as well as a formulation for use and treating human patients with infections. The invention focuses on treating patients with viral infections where the infection produces a cytokine storm. In particular, the infection results in the generation of IL-6 cytokines. An infection may be an infection with a virus commonly referred to as the coronavirus or COVID-19 which is SARS-COV-2.

The data provided in the examples was generated in connection with mouse adapted Ebola virus. However, conceptually the invention works with any virus that results in the generation of a cytokines storm.

In accordance with the method or the use of the formulation the patient is first diagnosed with a viral infection which is capable of producing a cytokines storm. If the diagnosis can be carried out in a number of different ways. For example, with RT-PCR or medical imaging including x-ray imaging can be used where in the lungs of the patient or examined for images which are characteristic of a particular type of viral infection.

Once the patient is diagnosed, a therapeutically affective amount of an anti-IL-6 antibody is administered to the patient. The antibody is allowed to bind cytokine molecules directly there by modulating down the cytokine storm in the patient. The antibodies may be embedded in biocompatible polymers and then formulated into an injection which can be administered intramuscularly or subcutaneously.

Measuring IL-6 Levels

Serum or plasma levels of IL-6 are quantitatively measured using a standard enzyme immunoassay (EIA of ELISA) kit that contains all the necessary reagents to perform the assay.

The assay employs an antibody specific for human IL-6, referred to as the capture antibody, that is immobilized onto the wells of a standard 96-well plate, although the capture antibody may also be stably coated on slides or beads, such as a Bio-Plex® assay (BioRad, Hercules, CA, USA), or any other solid support.

To perform the assay, known quantified standards, control value standards, and samples to be measured are pipetted onto the solid support whereby the IL-6 in the standards and controls, and if present in the samples, is bound to the wells, beads, or other solid support, by the capture antibody. After a suitable incubation period, most usually one to two hours, the wells are washed with a mild detergent solution to remove any excess serum or plasma proteins, after which biotinylated anti-human IL-6 antibody is added, also referred to as the detection antibody. After a suitable incubation period, usually one to two hours, the unbound detection antibody is removed by washing, after which HRP-conjugated streptavidin is pipetted to the wells. After a suitable incubation period, usually one hour, the excess HRP-conjugated streptavidin is removed by washing the wells with a mild detergent, after which a TMB substrate solution is added to the wells and color develops in proportion to the amount of IL-6 bound. After an appropriate amount of time, usually thirty minutes, a dilute solution of acid (the Stop Solution) is added to stop the reaction and change the color of the solution in the well from blue to yellow. The intensity of the yellow color is then measured using a spectrophotometer at 450 nm and the concentration of the samples are calculated using the values from the standard curve of known quantified standards and control value standards.

Dosing

A therapeutically effective dose of anti-IL-6 antibody will need to be determined on a patient-specific basis, preferably in conjunction with measuring a therapeutic effect by clinical signs, chest imaging, or by measuring the level of IL-6 in the patient's serum. The therapeutically effective dose of anti-IL-6 antibody can be expected to be in the range of 1 mg/Kg to 20 mg/Kg given via intravenous, subcutaneous or intramuscular routes of administration at intervals ranging from weekly to once every 6 weeks. Currently approved dosing is 11 mg/Kg given intravenously over the period of one hour with the administration repeated every three weeks. A larger initial dose could be given with the controlled release formulation of the invention with only a fraction of that dose being free, unencapsulated antibody. For example, a dose of 40 mg/Kg could be injected by a subcutaneous or intramuscular route wherein only 25% of the dose was free unencapsulated antibody. The remainder of the dose could comprise 25% set to release 8 hours after administration, 25% set to release 16 hours after administration, and 25% set to release 24 hours after administration.

In connection with the present invention the doses can be administered multiple times. However, it is preferable to administer a single dose and allow the antibody to be released gradually over time from the controlled release microparticles.

Larger or smaller doses can be administered initially. Further, the microparticles can be designed to release the antibody over hours, days, or weeks. The formulation can be designed so that antibody is released gradually over time or released in phases. The basic concept of the invention is to provide some initial antibody to modulate down the effect of cytokines and thereafter gradually release additional antibody so as to keep the cytokine level under control without completely eliminating the effects of any cytokines circulating in the blood.

Diagnosing

Two broad testing modalities are available to diagnose COVID-19: Reverse Transcriptase Polymerase Chain Reaction (RT-PCR) and chest imaging.

RNA from clinical samples or control cultures is extracted using commonly available reagents, for example, RNAzol® (Sigma-Aldrich, St. Louis, Missouri, USA), and purified using commonly available kits, for example QIAamp® viral RNA mini kit (QIAGEN, Valencia, CA, USA). Purified RNA is quantitated using, for example, a NanoDrop™ 2000 spectrophotometer system (ThermoFisher, San Jose, CA, USA).

For genomic sequencing, an RNA library is prepared using, for example, a TruSeq Stranded Total RNA Kit (Illumina, San Diego, CA, USA). Sequencing is performed on, for example, an Illumina Nextseq 500 platform producing on average a total of 150 million reads with approximately 150 base pairs per sample. Sequences are trimmed and qualified reads are mapped and aligned with a SARS-COV-2 reference sequence. Mutations are noted and a phylogenetic tree is created to track clustering and branching of possible new genetic variants.

For the analysis of specific genes using RT-PCR, RNA is reverse transcribed into cDNA using, for example, a High Capacity cDNA kit (ThermoFisher, San Jose, CA, USA). The cDNA is amplified using the PCR technique with forward and reverse primers that are specific for a certain region or gene of SARS-COV-2, for example the nucleoprotein (NP) gene. PCR reagents and conditions, including primer sequences, enzymes and thermocycling temperatures and times, are readily and freely available in the literature and/or from various reagent vendors, for example ThermoFisher, San Jose, CA, USA. Amplified fragments of DNA are measured for size (resolved) using, for example, agarose gel electrophoresis, the reagents and equipment for which are readily available from various manufacturers.

Quantification of RNA is also performed using the technique of RT-PCR wherein RNA is reverse transcribed into cDNA that is then directly amplified using primers specific for a certain region, gene, or set of genes of SARS-COV-2, such as the nucleoprotein, in accordance with recommended thermocycler times and temperatures. As the PCR evaluation proceeds, amplified DNA fragment levels are measured by the inclusion of a specific dye, for example SYBR Green (QIAGEN, Valencia, CA, USA), and quantified relative to the measure of an internal control or 'house-keeping' gene, for instance glyceraldehyde-3-phosphate dehydrogenase (GAPDH).

Chest radiographs and computer axial tomographic (CT) imaging can also be used to diagnose COVID-19. Relatively early findings on chest radiograph include a "ground glass" appearance over the lung fields. CT imaging can be used to document early and late stage progression of COVID-19.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

A BALB/c mouse model was used to compare the effect of anti-IL-6 antibody and anti-IL-6R antibody administered intraperitoneally to BALB/c mice see mice in the context of acute Ebola infection.

This model was chosen because Ebola is known to cause the elaboration of cytokines and that the mechanism of death associated with Ebola infection is in part due to cytokine storm. The experimental design utilized seven groups of ten mice per group. Group One was a vehicle control where no active agent was given. Group Two received a 400 µg intraperitoneal dose of IL-6 antibody 24 hours after the intraperitoneal administration of mouse adapted Ebola virus (maEBOV). Group Three received anti-IL-6 antibody (In VivoMAb anti-mouse IL-6) 48 hours after the administration of Ebola virus. Group Four received anti-IL-6 antibody 72 hours after inoculation with Ebola virus. Group Five received anti-IL-6R (In VivoMAb anti-mouse IL-6R) antibody 24 hours after Ebola infection. Group Six received anti-IL-6R antibody 48 hours after Ebola infection and Group Seven received anti IL-6R antibody 72 hours after the mice were infected with mouse adapted Ebola virus. The experiment design is described in Table 1.

TABLE 1

Experiment design.

| Group | N (male:female = 50%:50%) | Test Article | Dosing Regimen | Challenge Dose-Plaque Forming Units of maEBOV (PFU) |
|---|---|---|---|---|
| 1 | 10 | Dilution Buffer Vehicle, intraperitoneal administration | First dose 24 hours post challenge, subsequent doses Q72 hours | 100 PFU |
| 2 | 10 | Anti-mouse-IL-6 mAb, 400 µg intraperitoneal administration | First dose 24 hours post challenge, subsequent doses Q72 hours | 100 PFU |
| 3 | 10 | | First dose 48 hours post challenge, subsequent doses Q72 hours | 100 PFU |
| 4 | 10 | | First dose 72 hours post challenge, subsequent doses Q72 hours | 100 PFU |
| 5 | 10 | Anti-mouse-IL-6R mAb, 400 µg intraperitoneal administration | First dose 24 hours post challenge, subsequent doses Q72 hours | 100 PFU |
| 6 | 10 | | First dose 48 hours post challenge, subsequent doses Q72 hours | 100 PFU |
| 7 | 10 | | First dose 72 hours post challenge, subsequent doses Q72 hours | 100 PFU |

Figure 5:
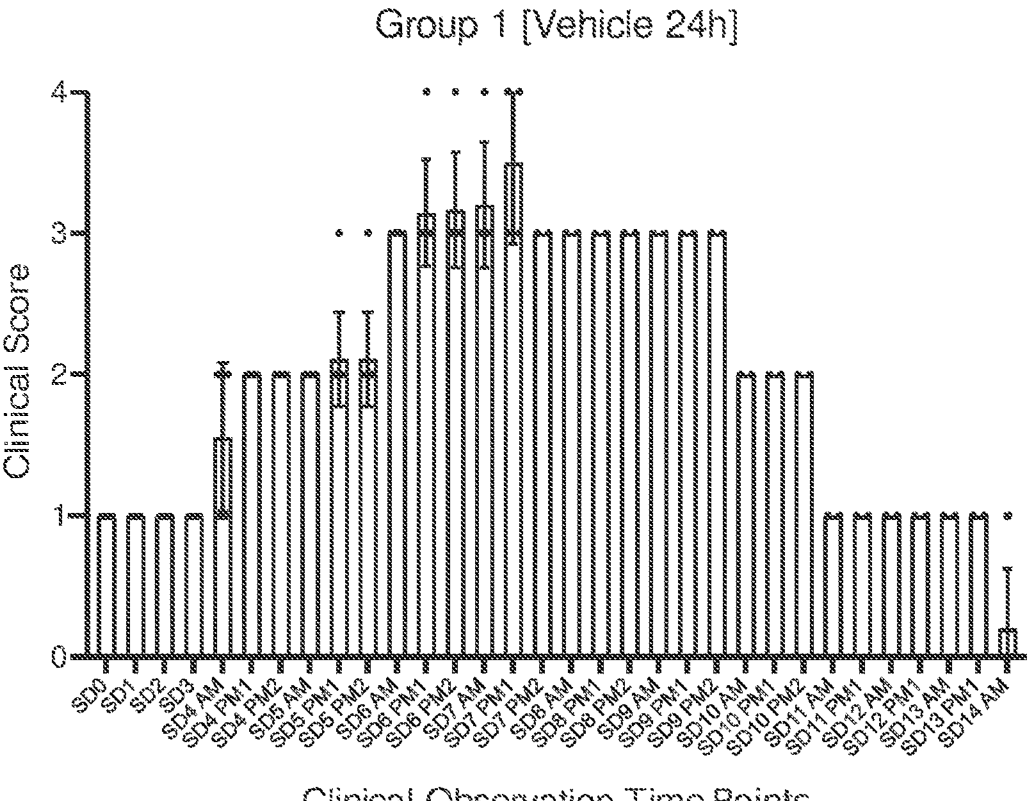
FIG. 5 Shows Clinical observations beginning on the day of maEBOV challenge for the vehicle control group.

These animals were followed for 14 days and clinical observations were made on a regular basis throughout the 14-day observation period using a scale described in Table 2. Final data display shows Kaplan-Meier survival curves in FIGS. 1-4, a vehicle control clinical observation histogram FIG. 5 and clinical observation histograms in FIGS. 6, 7, 8, 9, 10 and 11 for the different treatment antibodies and the different treatment times those agents were administered relative to the time of mouse adapted Ebola (maEBOV) challenge. In all cases, the animals received an intraperitoneal injection of anti-IL-6 antibody or anti-IL-6R antibody in an amount of 400 micrograms either 24, 48 or 72 hours after they received an intraperitoneal injection of 100 particle forming units (PFU) of mouse adapted Ebola virus.

TABLE 2

Quantitative Assessment of Pain and Distress

| Scale | Description of Animal |
|---|---|
| 1 | Healthy |
| 2 | Lethargic and/or ruffled fur (triggers a 2$^{nd}$ observation) |

TABLE 2-continued

Quantitative Assessment of Pain and Distress

| Scale | Description of Animal |
|---|---|
| 3 | Ruffled fur, lethargic and hunched posture, orbital tightening (triggers a 3$^{rd}$ observation) |
| 4 | Ruffled fur, lethargic and hunched posture, orbital tightening, reluctance to move when stimulated, paralysis OR ≥ 20% weight loss (requires immediate euthanasia) |

Figure 2:
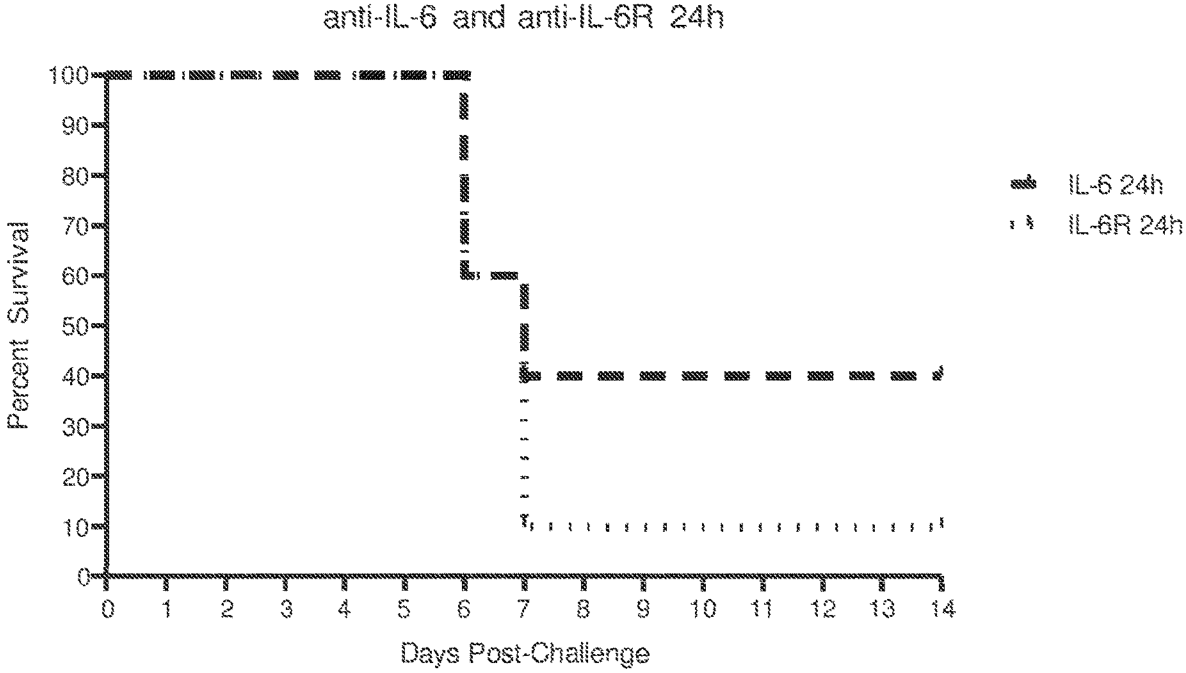
Figure 3:
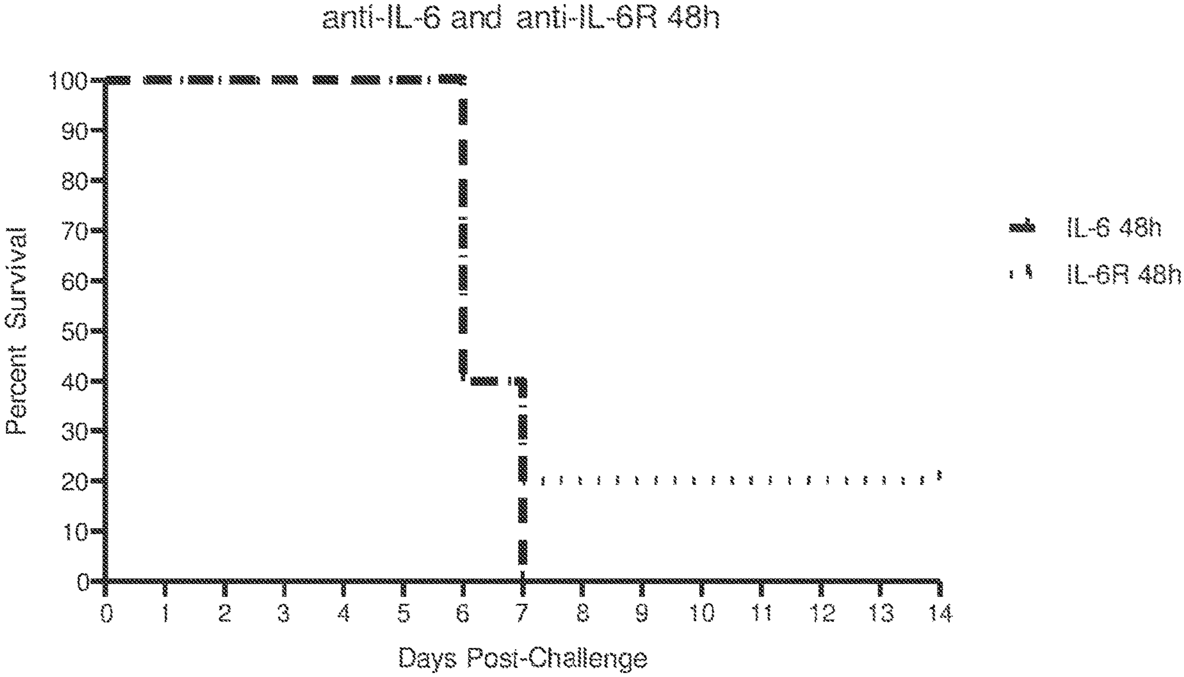
FIG. 3 Shows Kaplan-Meier Survival Curves after treatment with either anti-IL-6 antibody or anti-IL-6R antibody beginning 48 hours after maEBOV challenge.

An analysis of this data shown in FIG. 2 indicates that four out of ten mice receiving anti-IL-6 antibody twenty-four hours after Ebola administration survived for 14 days and that one out of the 10 mice receiving anti-IL-6R antibody survived for 14 days given 24 hours after maEBOV exposure.

Figure 6:
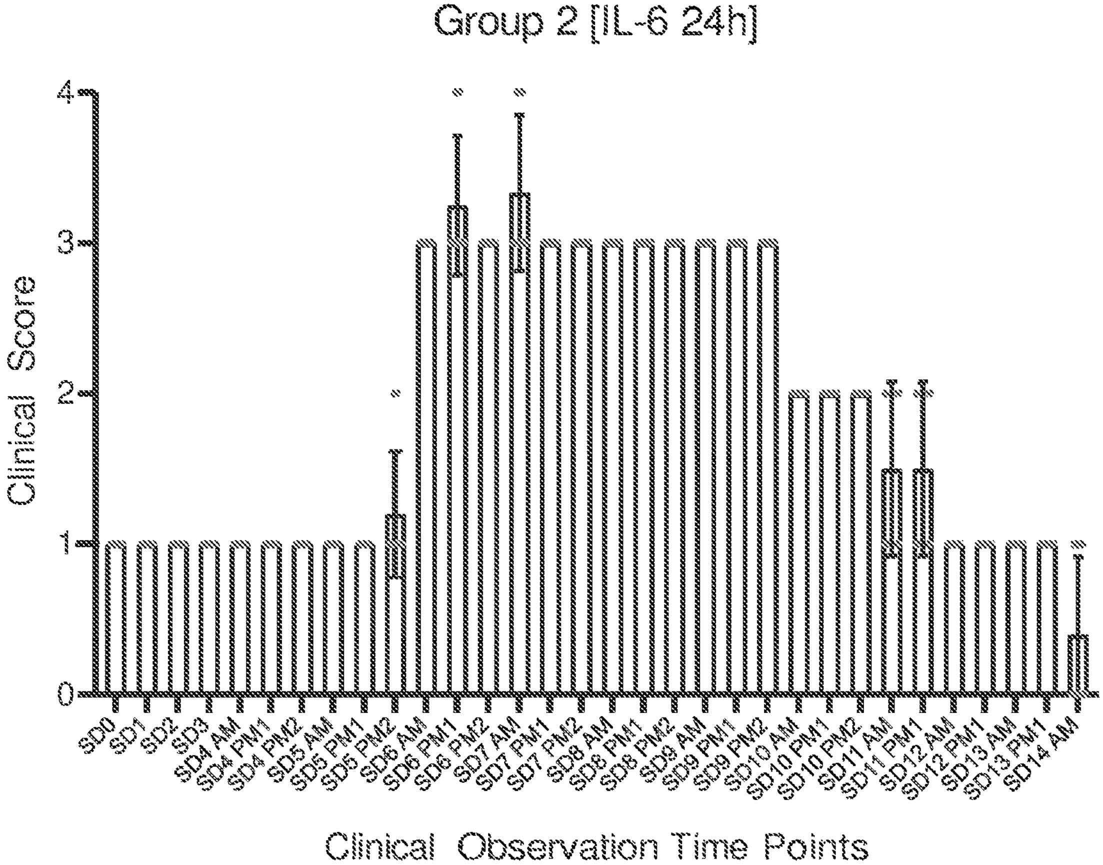
FIG. 6 Shows clinical observations beginning on the day of maEBOV challenge for the group receiving anti-IL-6 antibody 24 hours after challenge.
Figure 7:
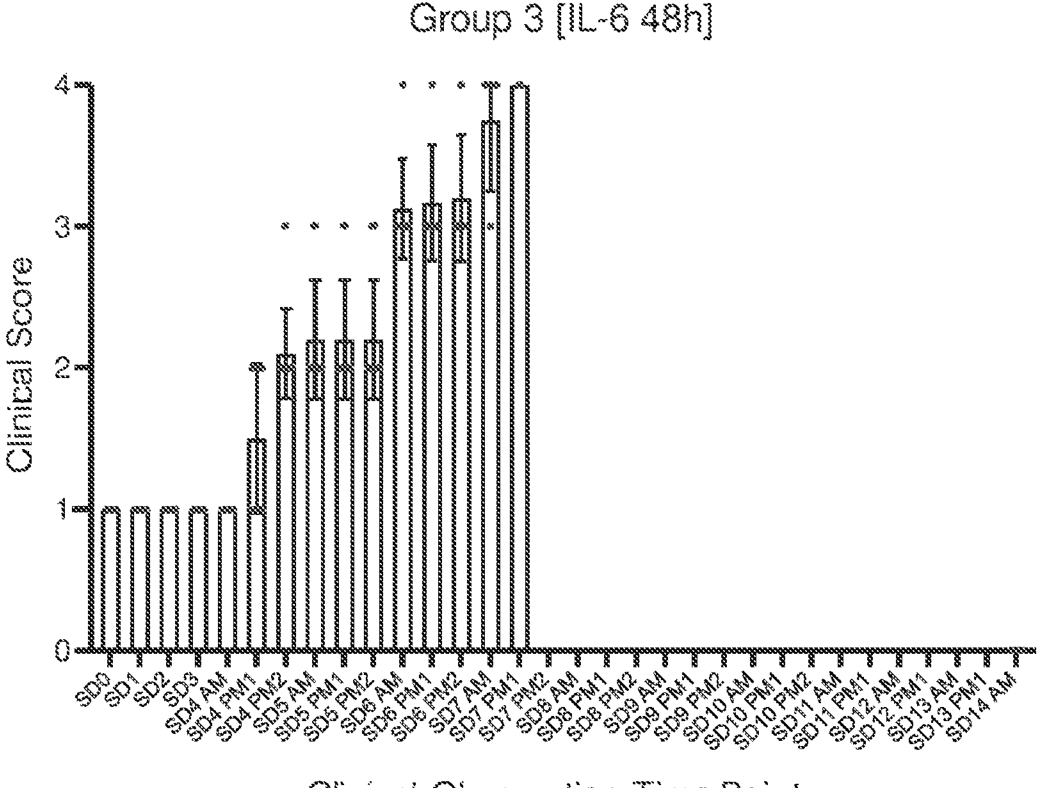
FIG. 7 Shows clinical observations beginning on the day of maEBOV challenge for the group receiving anti-IL-6 antibody 48 hours after challenge.
Figure 8:
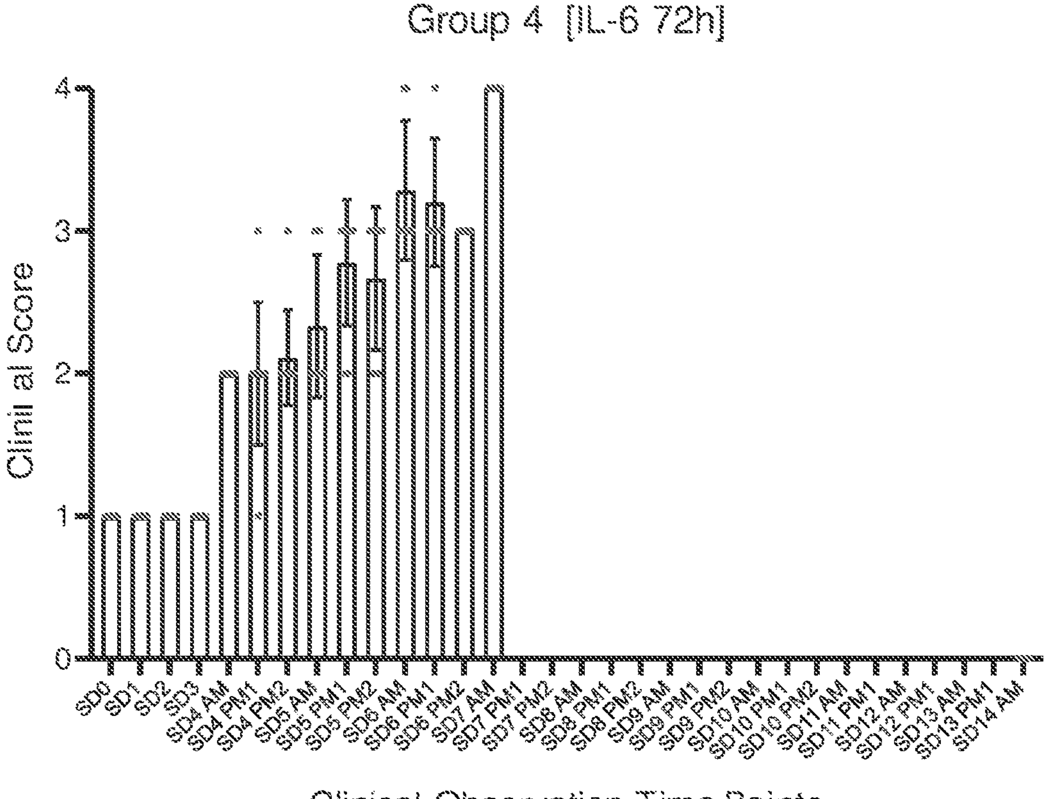
FIG. 8 Shows clinical observations beginning on the day of maEBOV challenge for the group receiving anti-IL-6 antibody 72 hours after challenge.
Figure 9:
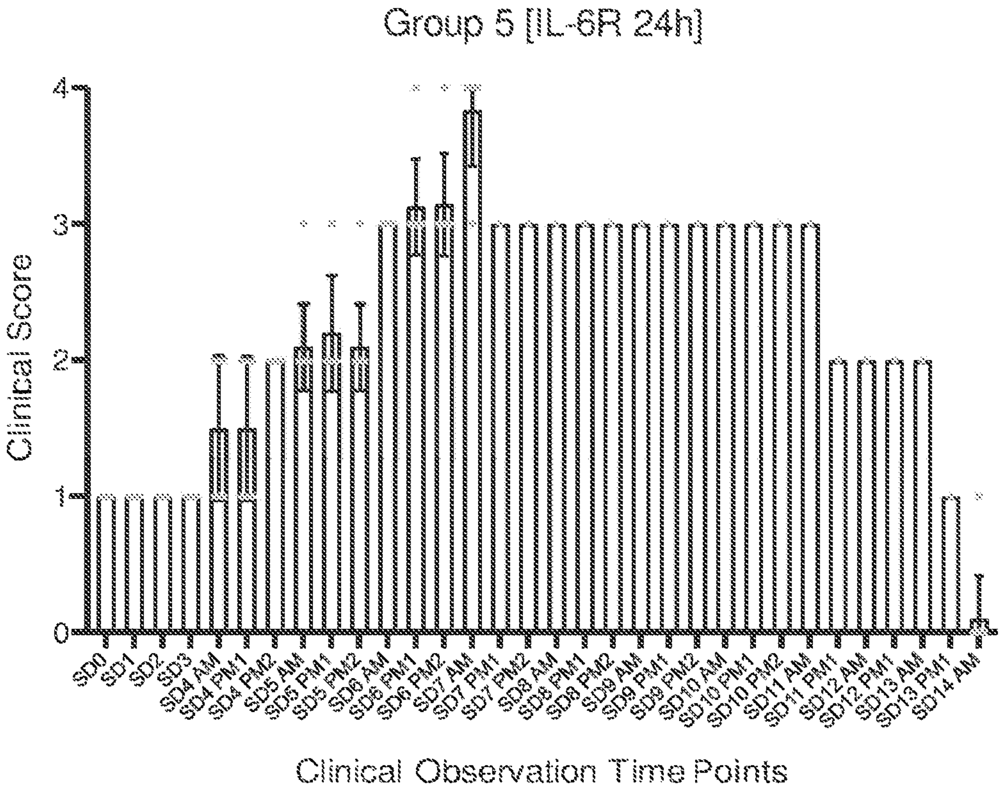
FIG. 9 Shows clinical observations beginning on the day of maEBOV challenge for the group receiving anti-IL-6R antibody 24 hours after challenge.
Figure 10:
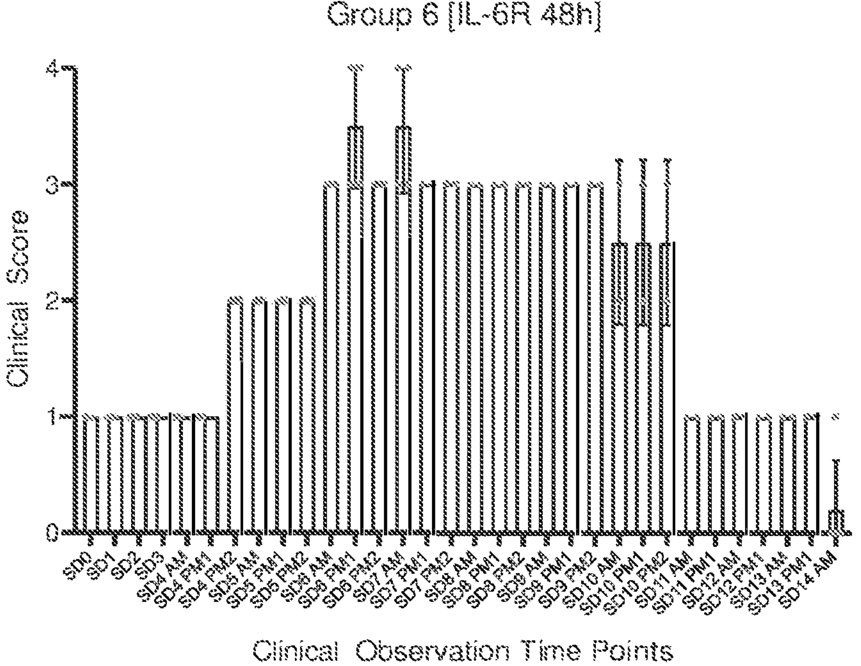
FIG. 10 Shows clinical observations beginning on the day of maEBOV challenge for the group receiving anti-IL-6R antibody 48 hours after challenge.
Figure 11:
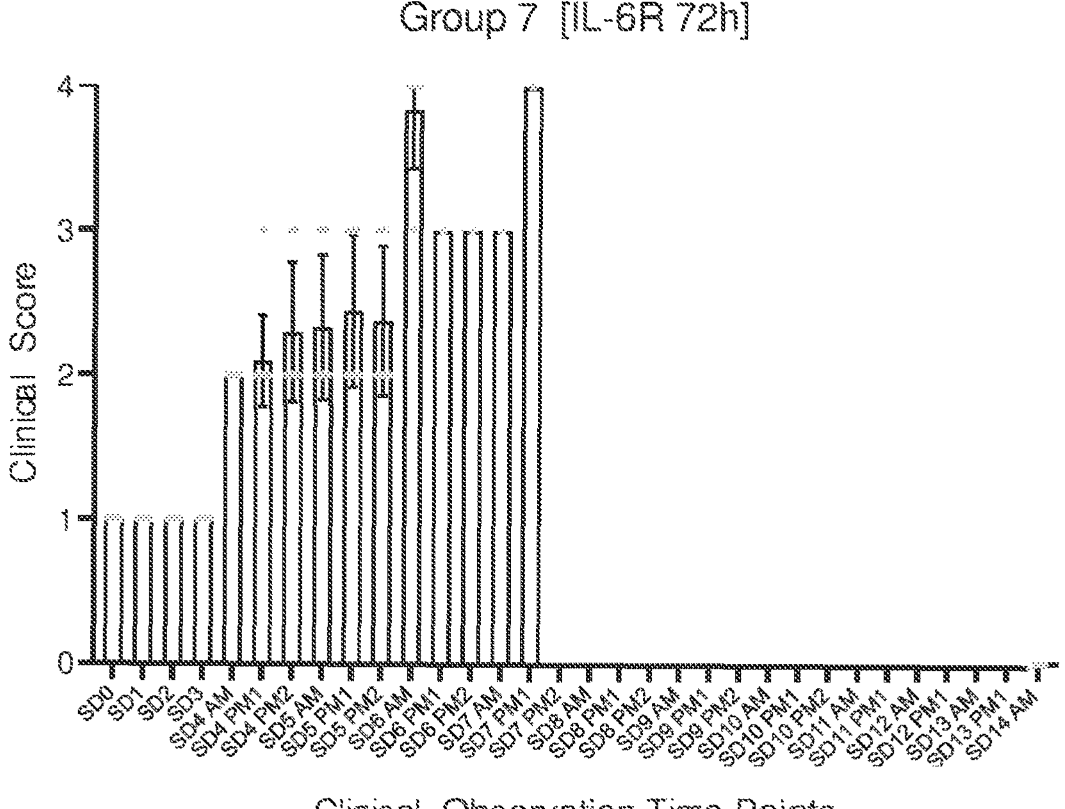
FIG. 11 Shows clinical observations beginning on the day of maEBOV challenge for the group receiving anti-IL-6R 72 hours after challenge.

FIG. 6 shows that in the group receiving anti-IL-6 antibody 24 hours after Ebola administration that the mice were deemed to be healthy by clinical observation through the first two (out of three) clinical observations made on Study Day 5. In contrast, as shown in FIG. 9 the mice receiving anti-IL-6R antibody began to exhibit symptoms of Ebola infection after study day three.

This data suggests that anti-IL-6 antibody may provide benefit early during the course of cytokine storm in the context of viral infection. The development of micro encapsulated anti-IL-6 and anti-IL6R antibody to be given together or separately to patients presenting with COVID-19 infection or infection with other viruses producing cytokine storm could provide a mechanism for intramuscular delivery of these potentially important therapeutic agents in the context of a pandemic where management of intravenous lines in a controlled setting is difficult or impossible.

The use of intramuscular or subcutaneous injection of these agents in a controlled release format similar to the area under the curve pharmacokinetics achieved by intravenous delivery could be a breakthrough approach in allowing the most number of people to be treated early during the disease, without requiring intravenous access typically only available in a hospital or other complex clinic type of environment.

Example 2

Virus Strain

For in-vivo experiments, a well-characterized mouse-adapted Ebola virus (maEBOV) stock (Bray et al., 1998; Lane et al., 2019), was used for all studies. All work involving infectious maEBOV was performed in a biosafety level (BSL) 4 laboratory, registered with the Centers for Disease Control and the Prevention Select Agent Program for the possession and use of biological select agents.

Animal Studies

Animal studies were conducted at University of Texas Medical Branch (UTMB) at Galveston in compliance with the Animal Welfare Act and other federal statutes and regulations relating to animals and experiments involving animals and adhered to principles stated in the "Guide for the Care and Use of Laboratory Animals." The facility where this research was conducted (UTMB) is fully accredited by the Association for the Assessment and Accreditation of Laboratory Animal Care International and has an approved OLAW Assurance. The BALB/c mice used in these studies were sourced from our colony at UTMB. We conducted these studies in BALB/c mice challenged with 100 plaque forming units (PFU) of mouse-adapted Ebola virus (maEBOV) (Lane et al., 2019) delivered by i.p. administration. A control group of mice received maEBOV plus the antibody vehicle alone (n=36).

Figure 12:
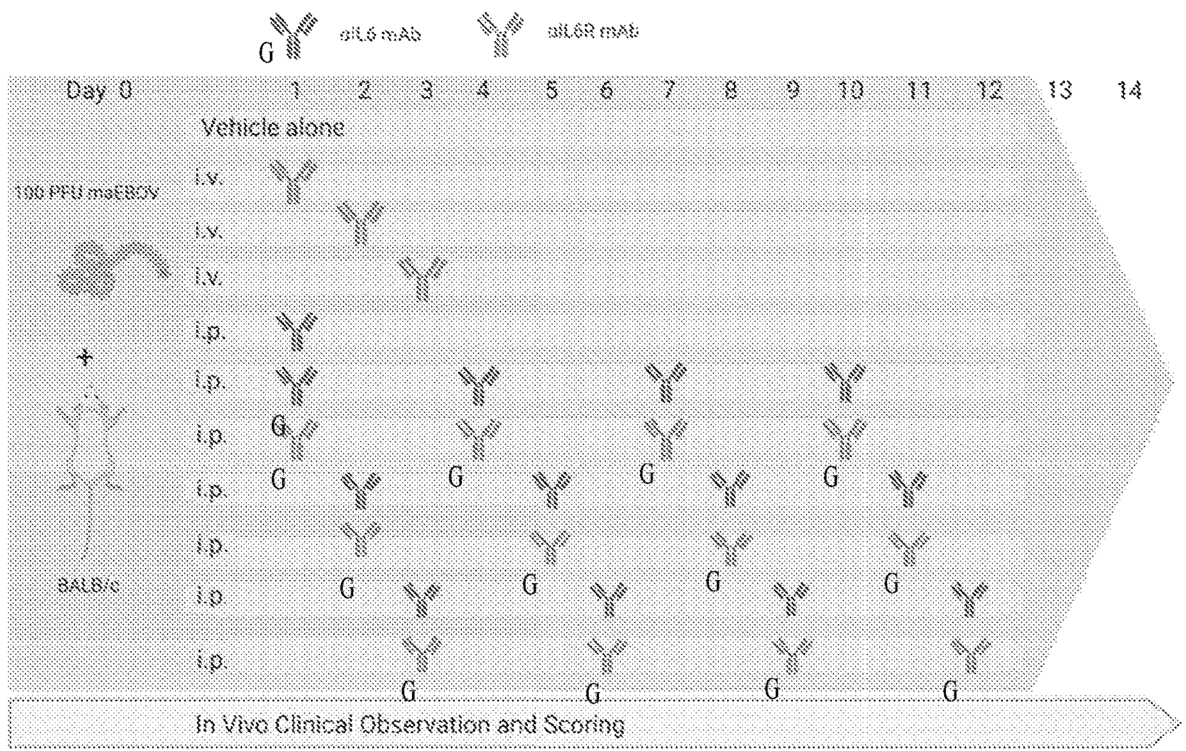
FIG. 12 is a diagram showing a dosing schedule for IL-6 and IL-6R antibodies used in Example 2.

Experimental groups of 10 mice each were administered anti-IL-6 mouse monoclonal antibody (BioXCell, BE0046, Lebanon, NH) or anti-IL-6R mouse monoclonal antibody (BioXCell, BE0047) 100 ug in a saline vehicle via intravenous (i.v.) administration, or 400 ug via intraperitoneal (i.p.) injection at either 24, 48, or 72 hours post-challenge. Antibody dosing was performed once (for the i.v. group) or continued at 72-hour intervals (for the i.p. groups) for a total of four doses over the 14-day study period as summarized in FIG. 12.

In-Vivo Clinical Observations and Scoring

Individual mice were examined daily and scored for their clinical appearance and health as previously described (Lane et al., 2019). Briefly, mice were assigned a score of 1=Healthy; score 2=Lethargic and/or ruffled fur (triggers a second observation); score 3=Ruffled fur, lethargic and hunched posture, orbital tightening (triggers a third observation); score 4=Ruffled fur, lethargic, hunched posture, orbital tightening, reluctance to move when stimulated, paralysis or greater than 20% weight loss (requires immediate euthanasia) and no score=deceased (FIG. 19).

Statistical Methods

Descriptive and comparative statistics including arithmetic means, standard errors of the mean (SEM), Survival Kaplan-Meier plots and Log-rank (Mantel-Cox) testing, D'Agostino & Pearson test for normality, Area-Under-The-Curve and Z Statistics were calculated using R with data from Prism graph pad files. The clinical composite score data used to calculate the AUC measures were normally distributed. The significance of comparisons (P values) of AUC data was calculated using the Z statistic. P values <0.05 were considered statistically significant.

Results

Figure 16:
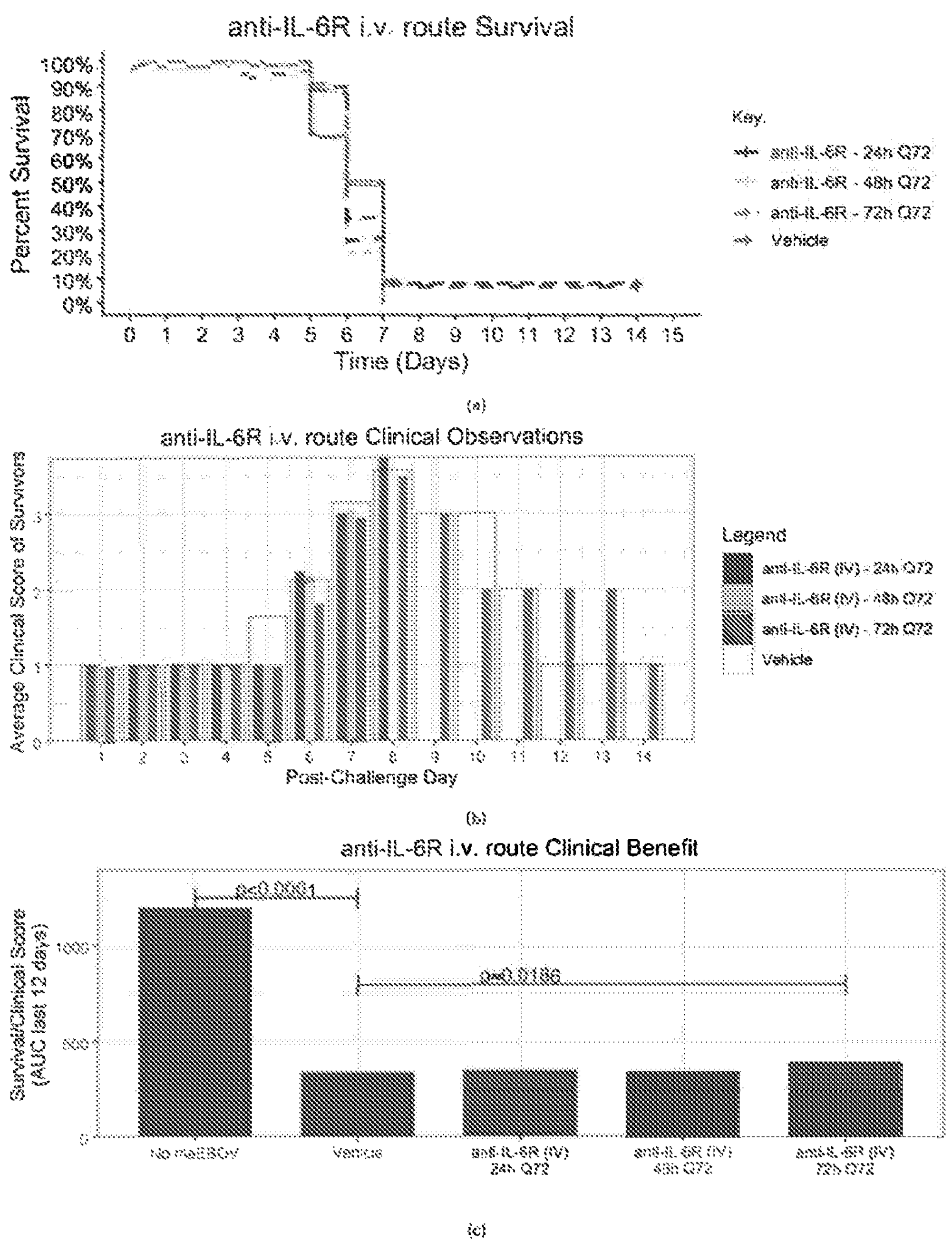
FIG. 16 consists of three different graphs 16 A 16 B and 16 C. Survival, Clinical Scores and AUC Survival/Clinical score for one i.v. dose anti-IL-6R. (16A) Kaplan Meier Plot of mouse survival receiving one i.v. dose of anti-IL-6R 24 post maEBOV challenge. The curves were not significantly different by Log-rank (Mantel-Cox) testing. (16B) Average Clinical scores for surviving mice receiving one i.v. dose anti-IL-6R 24 post maEBOV. SEM were <10% of the mean. Bottom Panel. (16C) A composite benefit metric was calculated as the AUC for the last 12 days of the quotient of survival and clinical score. The AUC for a group of healthy untreated mice (for example, 100% survival with a healthy clinical score of 1 observed for twelve days would be calculated as 1200).

Following maEBOV challenge, BALB/c mice were dosed i.v. with monoclonal antibody at 24, 48 or 72 hours post-challenge with a single dose of anti-IL-6R mAb i.v., or an initial i.p. dose of anti-IL-6 or anti-IL-6R mAb, followed by additional i.p. doses for three days at 72 hour intervals for a total of four doses. Mice where observed for 14 days. The survival and average clinical score for mice receiving a single i.v. dose of anti-IL-6R mAb is shown in FIG. 16.

Figure 14:
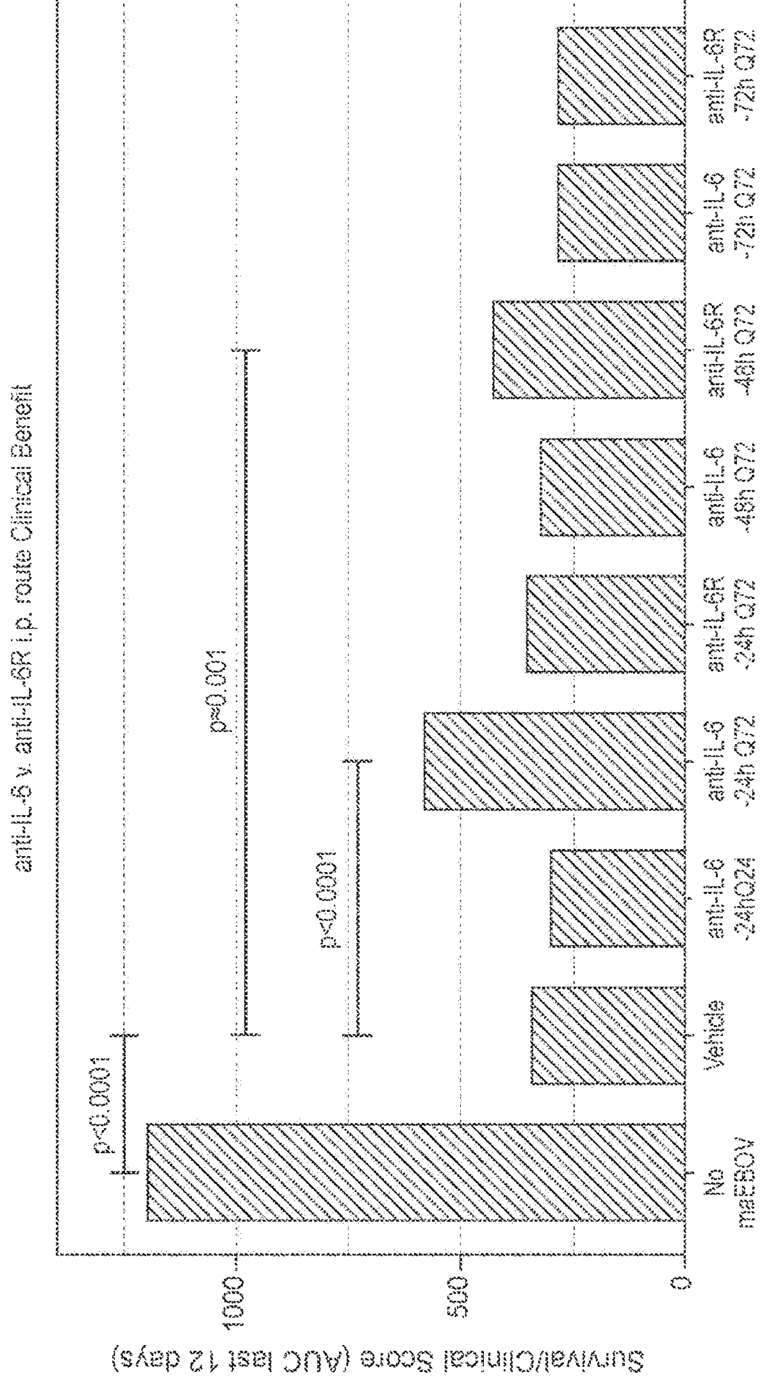
FIG. 14 is a graph showing the survival/clinical score versus different types of dosing. A clinical benefit metric was calculated as an area under curve for survival/clinical scores for 120 mice receiving a single or multiple i.p. doses of anti-IL-6 or anti-IL-6R mAb following maEBOV challenge 121 on day 0. The given p values are determined from the Z statistic calculated for each experimental condition.

The survival patterns for both treated and untreated groups following maEBOV challenge were statistically different and most untreated mice succumbed to maEBOV infection by day seven. Because neither survival score alone or average clinical score represented the overall possible clinical benefits of mAb treatment, a secondary composite outcome measure was calculated from the quotient of mouse survival and the average clinical score for each day, similar to that previously reported (Kaempf et al., 2019). We then summed these scores across the last 12 days of observation to create an AUC Survival/Clinical Score (FIG. 14). The Z statistic and significance level for this metric was calculated for each experimental condition.

The AUC Survival/Clinical Score showed a minor clinical benefit (P<0.01) when mice were given one 100 μg dose of anti-IL-6R mAb via central venous catheter at 72 hours after maEBOV challenge, relative to vehicle alone, using the experimental design described in FIG. 17.

Figure 13:
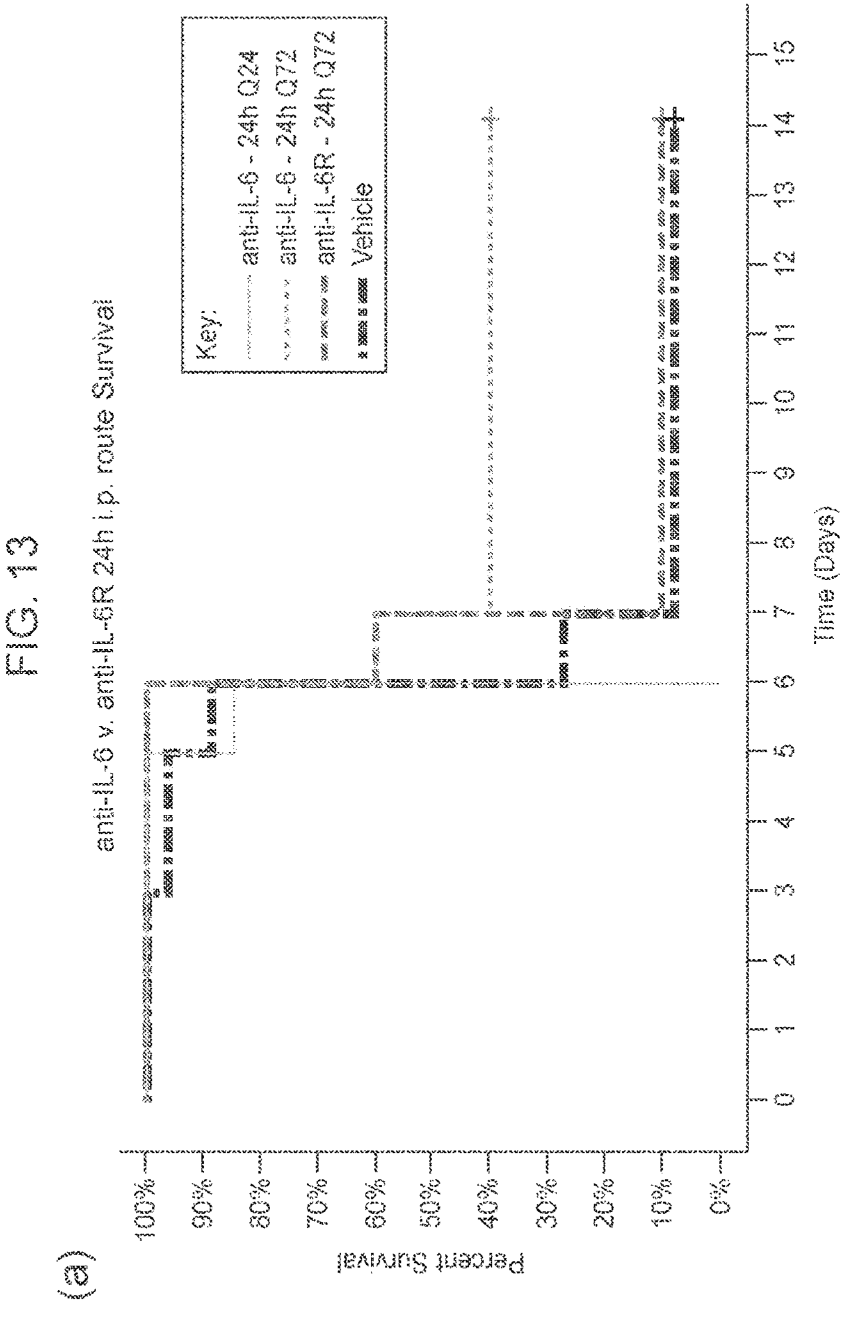
FIG. 13 consists of four graphs 13 A, 13 B, 13 C, and 13 D which graphs relate to the survival plots and average clinical scores for mice treated in accordance with example 2. Kaplan-Meier Survival Plots and Average clinical scores for a single or multiple intraperitoneal (i.p.) doses of anti-IL-6 or anti-IL-6R administered at 24, 48 or 72 hours following maEBOV challenge and then repeated every 72 hours for a total of four doses. The survival curves were significantly different by Log-rank (Mantel-Cox) testing ($P<0.05$). SEM were <10% of the mean.
Figure 13:
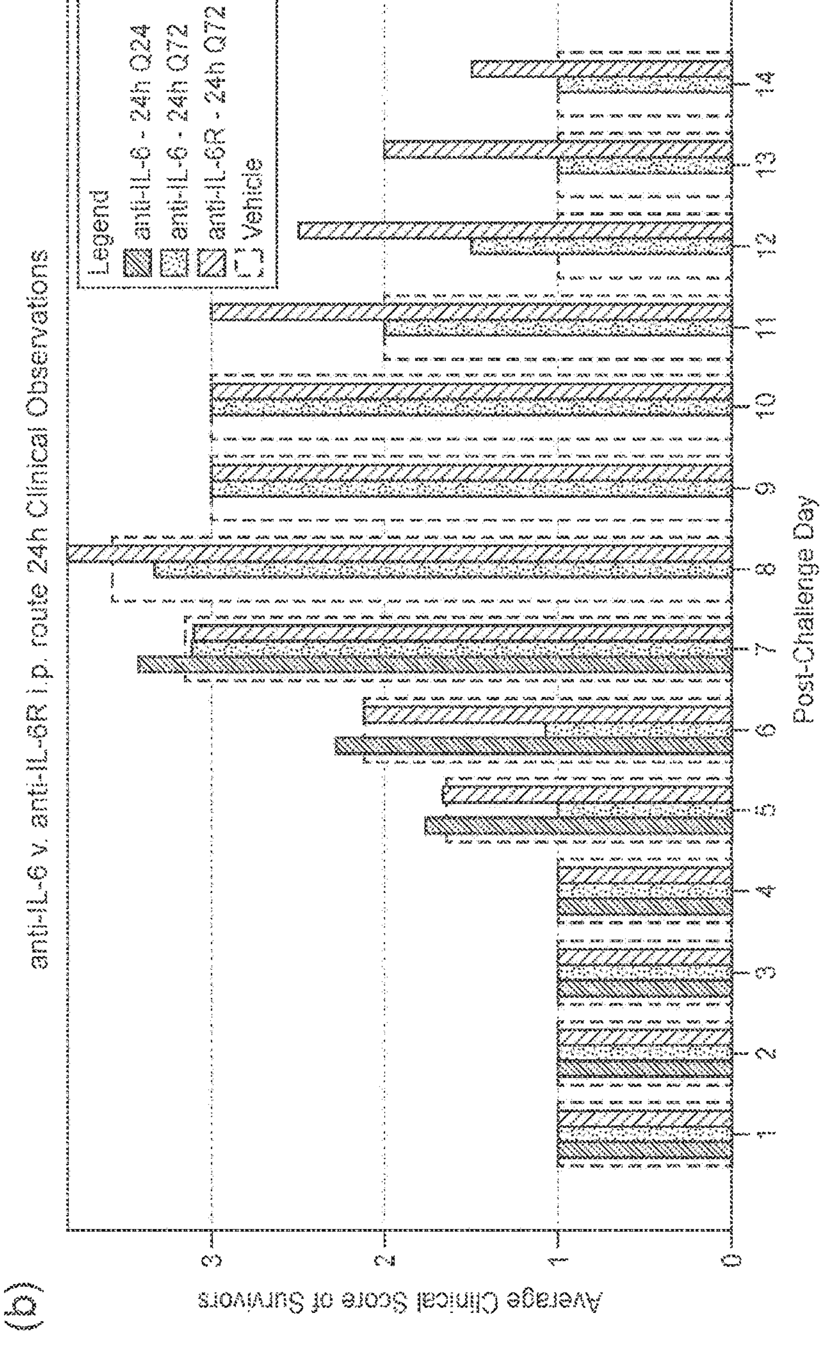
Figure 13:
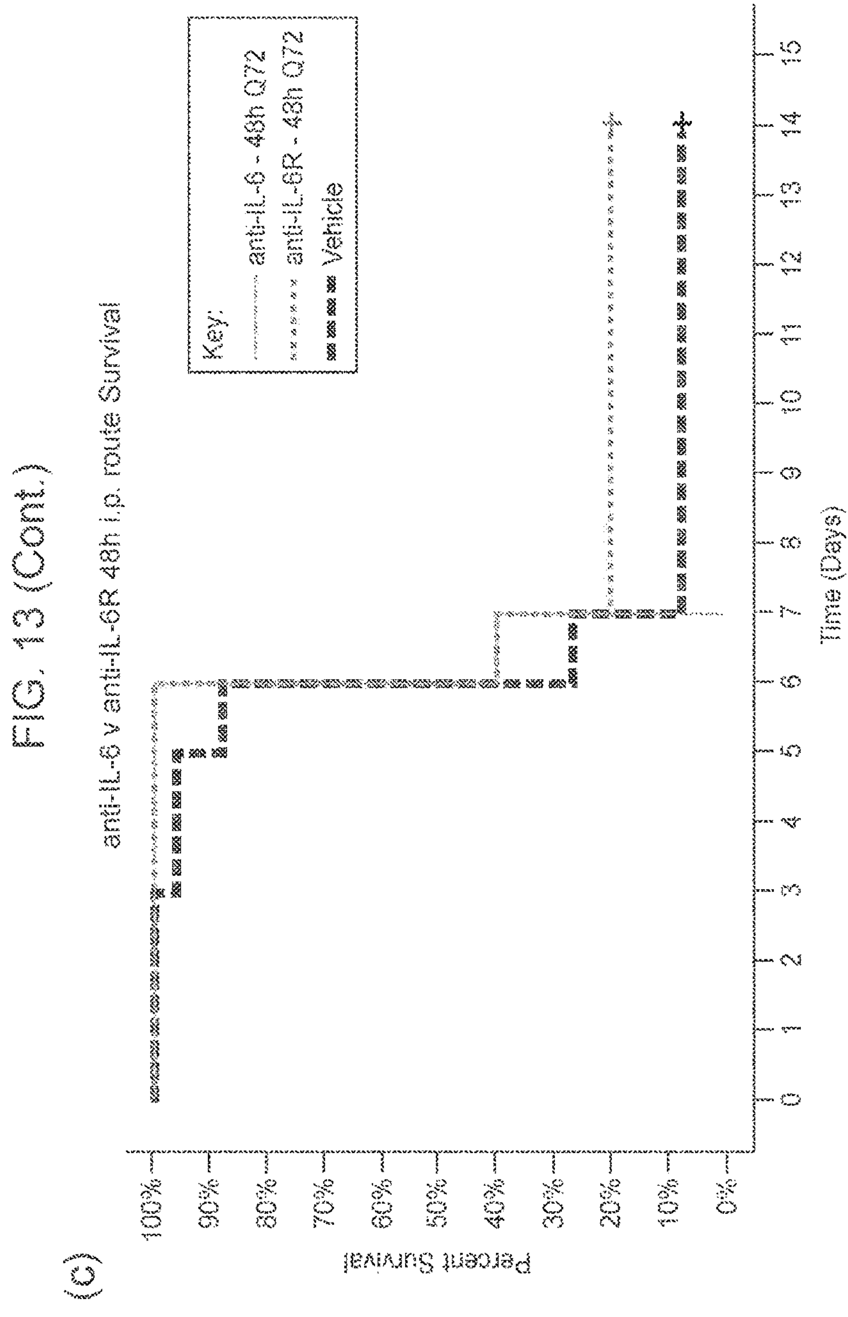
Figure 13:
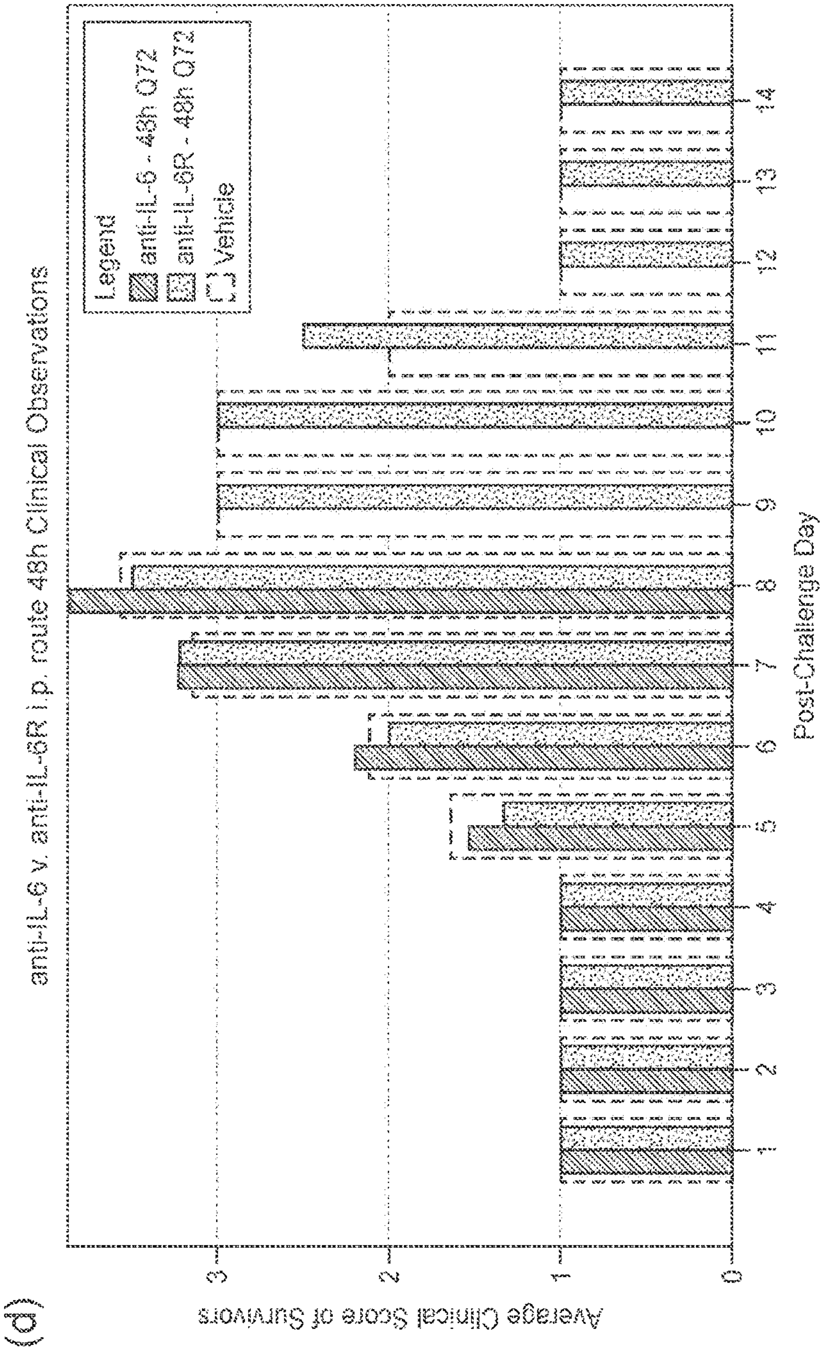
Figure 13:
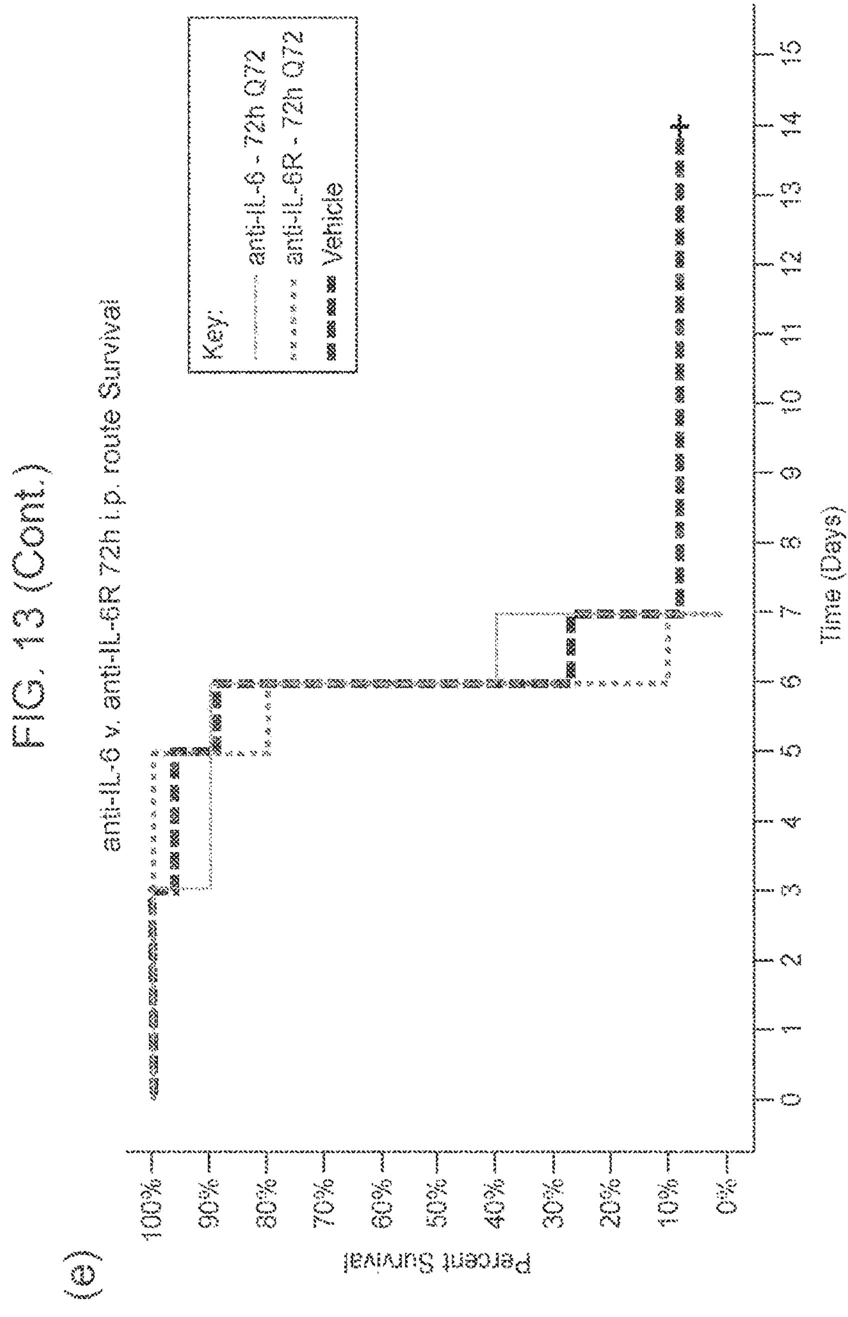
Figure 13:
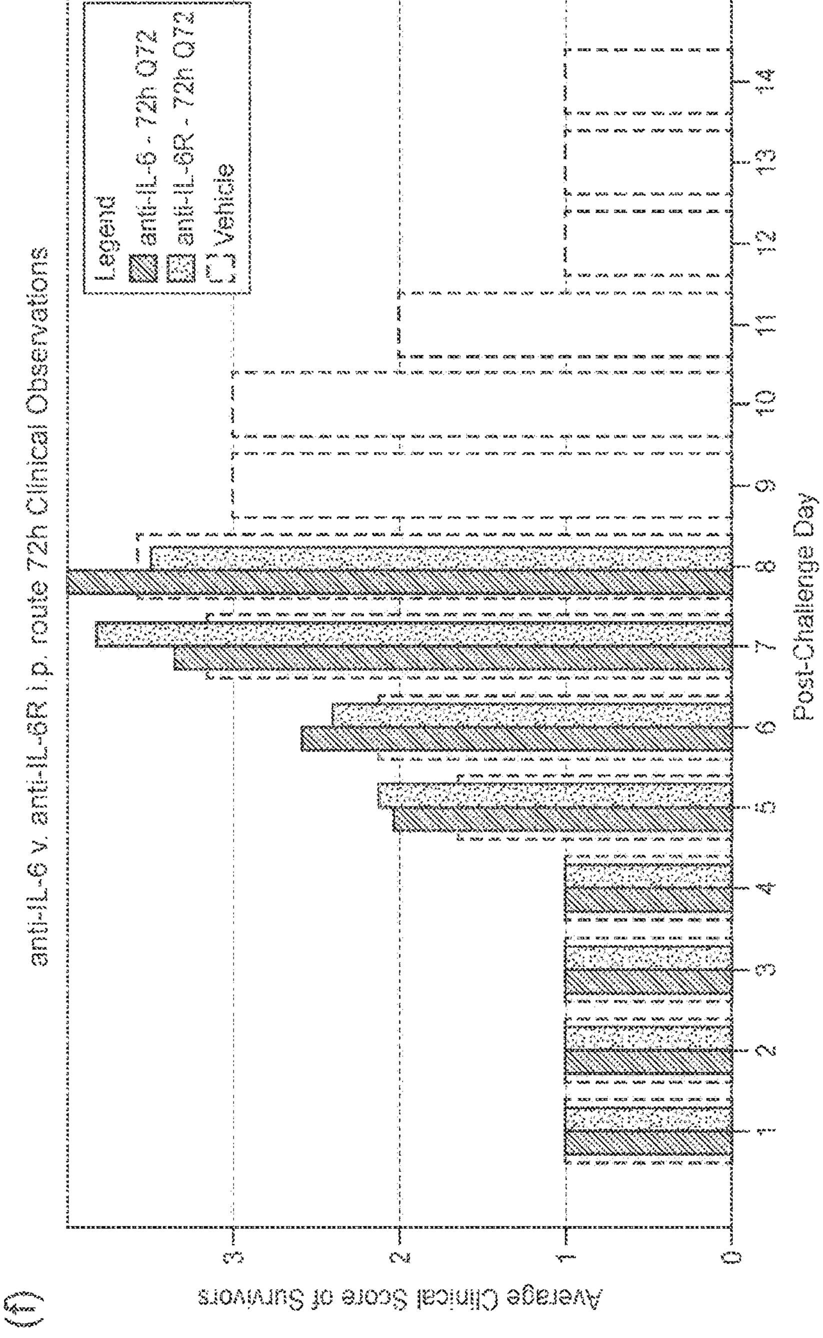

Since the maEBOV challenge was administered intraperitoneally and murine peritoneal macrophages represent a significant depot of cells (Cassado et al., 2015) able to produce IL-6 (Vanoni et al., 2017) following TLR activation, we next compared the activities of anti-IL-6 and anti-IL-6R mAb administered intraperitoneally following maEBOV challenge (FIGS. 13, and 14).

We observed significant differences in the AUC Survival/Clinical Score when anti-IL-6R mAb was administered 48 hours post maEBOV challenge and then repeated three times at 72-hour intervals.

The most significant effect on the AUC Survival/Clinical Score was seen when anti-IL-6 mAb was administered beginning at 24 hours post maEBOV challenge, and then repeated three times at 72-hour intervals.

Discussion

These data show that anti-IL-6 antibody therapy has a clinical advantage over anti-IL-6R mAb particularly when given early during the course of maEBOV infection. The observed clinical benefit is associated with incomplete blockade of IL-6 early during the course of the infection which allows some innate immune protection against the virus.

Although antibody blood levels were not obtained during the mouse studies described here, we present a pharmacokinetic model based on literature values (Sanofi, 2017; EUSA, 2015; Medesan et al., 1998) shown in FIG. 18. Simulated PK curves for each of the three experiments described is shown in FIG. 15.

Dosing anti-IL-6 mAb at 24 hours after challenge produced a clinical benefit, whereas dosing anti-IL-6R beginning at the same time point did not.

The shorter terminal half-life of anti-IL-6 mAb (T½=57 h) versus anti-IL-6R mAb (T½=223 h) explains why giving anti-IL-6 mAb early after infection provided the most observed clinical benefit.

Figure 15:
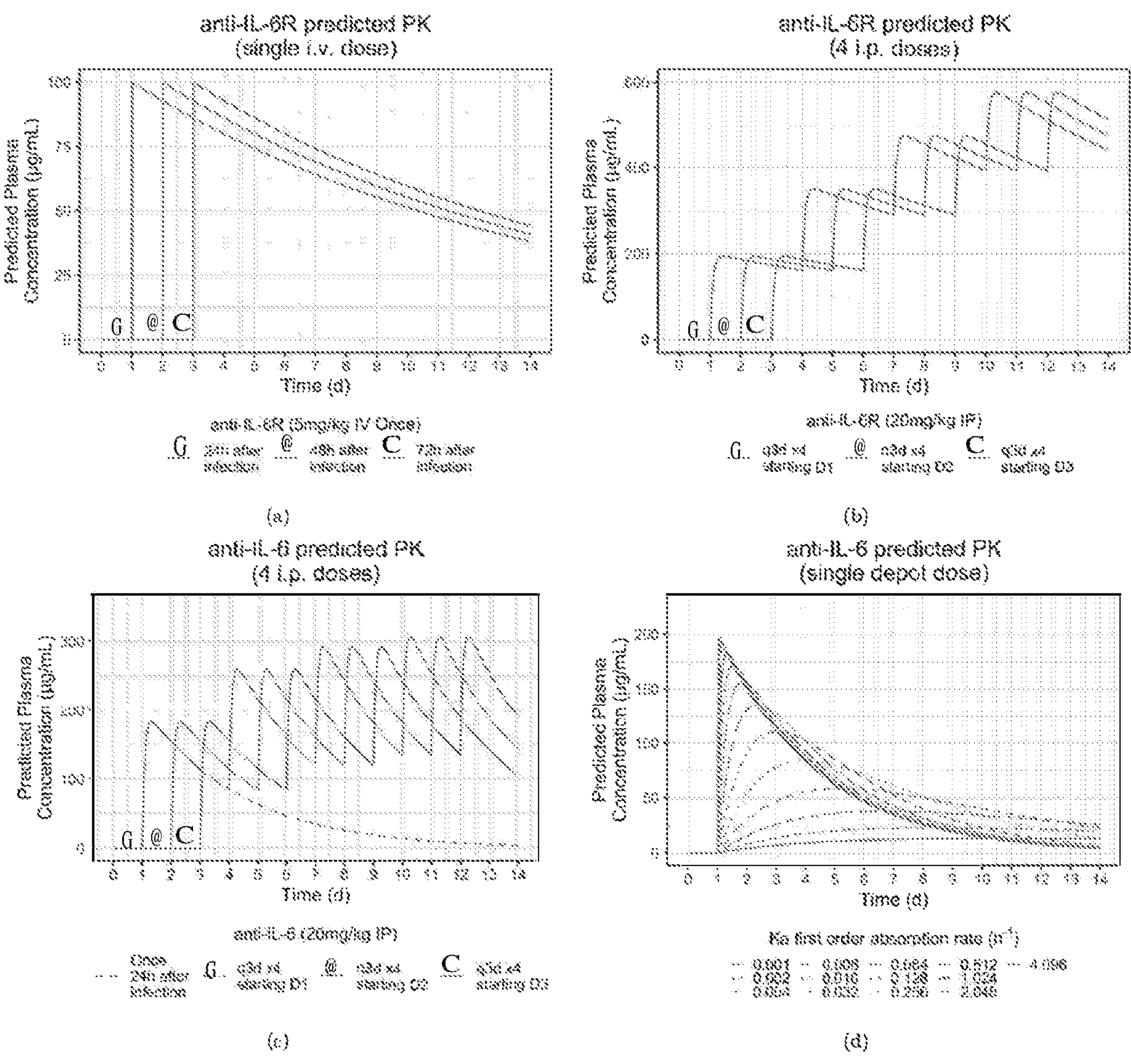
FIG. 15 that consists of graphs 15 A 15 B 15 C and 15 D which show simulated PK profiles for different routes of administration. Simulated PK profiles for i.v. and i.p. routes of administration based on literature PK parameters shown in in FIG. 19 were determined. Panels (15A) models the intravenous (i.v.) delivery experiment. Panels (15B) and (15C) model i.p. delivery experiments one and two. For each of these simulations, mice were dosed a total of four times at 72 hour intervals, beginning 24 hours after challenge. Panel (15D) models release profiles for simulated controlled release scenarios with different absorption rates as indicated by the listed Ka parameters.

As can be seen from the simulated PK profile in FIG. 15 (C), repeated dosing every 72 hours, beginning 24 hours after challenge, is predicted to maintain blood levels peaking at about 200 μg/ml. This contrasts with blood levels predicted after similar dosing of anti-IL-6R where the blood levels continue to increase over the study period. These differences seen in the simulated PK profiles may have allowed anti-IL-6 mAb to partially block IL-6, allowing innate immunity to develop, while still providing enough blockade to reduce the deleterious clinical effects of IL-6 as the study progressed.

In addition, it may be that the stoichiometry of anti-IL-6 blockade versus anti-IL-6R may favor achieving partial blockade early during the evolution of CRS given that the amount of IL-6 present may exceed the number of IL-6 receptors. It is also possible that IL-6 may act on other sites not blocked by anti-IL-6R mAb, and that this may yield a potential advantage of using anti-IL-6 mAb to treat CRS brought about by a viral infection.

The invention includes a controlled release formulation of anti-IL-6 mAb to obtain a clinically beneficial effect from the administration of anti-IL-6 mAb, anti-IL-6R mAb, or a combination of both, after a single injection early during the course of SARS-CoV-2 infection.

For example, FIG. 15 (D) shows various predicted controlled release PK profiles of anti-IL-6 mAb that could be achieved by using delivery systems producing different first order rates of delivery from an injection depot. Correlation of these release profiles with the AUC Survival/Clinical score described here in pre-clinical models shows those skilled in the art how to make a use a single dose treatment mitigating the effects of CRS on the host. A single dose, controlled release injectable formulation of anti-IL-6 mAb allows for treatment early during the diagnosis of COVID-19, allowing patients to begin receiving therapy early during the evolution of CRS, even before hospitalization.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

REFERENCES 1 (2020). Genentech's arthritis drug tocilizumab shows promise in covid-19 trial. *Clinical Trials Arena*

2 Ascierto, P. A., Fox, B. A., Urba, W. J., Anderson, A. C., Atkins, M. B., Borden, E. C., et al. (2020). Insights from immuno-oncology: the society for immunotherapy of cancer statement on access to il-6-targeting therapies for covid-19. *Journal for ImmunoTherapy of Cancer* 8, e000878. doi:10.1136/jitc-2020-000878

3 Bray, M., Davis, K., Geisbert, T., Schmaljohn, C., and Huggins, J. (1998). A Mouse Model for Evaluation of Prophylaxis and Therapy of Ebola Hemorrhagic Fever. *The Journal of Infectious Diseases* 178, 165 651-661. doi:10.1086/515386

4 Cassado, A. d. A., D'Império Lima, M. R., and Bortoluci, K. R. (2015). Revisiting mouse peritoneal macrophages: Heterogeneity, development, and function. *Frontiers in Immunology* 6, 225. doi:10.3389/fimmu.2015.00225

5 Chen, N., Zhou, M., Dong, X., Qu, J., Gong, F., Han, Y., et al. (2020). Epidemiological and clinical characteristics of 99 cases of 2019 novel coronavirus pneumonia in wuhan, china: a descriptive study.

6 *The Lancet* 395, 507-513. doi:10.1016/s0140-6736(20) 30211-7

7 Conti, P., Ronconi, G., Caraffa, A., Gallenga, C., Ross, R., Frydas, L., et al. (2020), Induction of pro-inflammatory cytokines (il-1 and il-6) and lung inflammation by coronavirus-19 (covi-19 or sars-cov-2): anti-inflammatory strategies. *Journal of biological regulators and homeostatic agents* 34. doi:10.23812/conti-e 8 Dienz, O. and Rincon, M. (2009). The effects of il-6 on cd4 t cell responses. *Clinical Immunology* 130, 27-33. doi: 10.1016/j.clim.2008.08.018

9 EUSA (2015). Drug approval package: Sylvant (siltuximab). *U.S. Food & Drug Administration*

10 Genentech (2014). Drug approval package: Actemra (tocilizumab) solution for subcutaneous injection. *U.S. Food & Drug Administration*

11 Gritti, G., Raimondi, F., Ripamonti, D., Riva, I., Landi, F., Alborghetti, L., et al. (2020). Use of siltuximab in patients with covid-19 pneumonia requiring ventilatory support. *medRxiv*

12 Herper, M. (2020). Closely watched arthritis drug disappoints as a covid-19 treatment, studies show. *STAT*

13 Herst, C., Burkholz, S., Sidney, J., Sette, A., Harris, P., Massey, S., et al. (2020). An effective ctl peptide vaccine for ebola zaire based on survivors' cd8+ targeting of a particular nucleocapsid protein epitope with potential implications for covid-19 vaccine design. Vaccine doi.org/10.1016/j.vaccine.2020.04.034

14 Huang, C., Wang, Y., Li, X., Ren, L., Zhao, J., Hu, Y., et al. (2020a). Clinical features of patients infected with 2019 novel coronavirus in wuhan, china. *The Lancet* 395, 497-506. doi:10.1016/80140-6736(20)19030183-5

15 Huang, C., Wang, Y., Li, X., Ren, L., Zhao, J., Hu, Y., et al. (2020b). Clinical features of patients infected with 2019 novel coronavirus in wuhan, china.

The Lancet 395, 497-506. doi.org/10.1016/S0140-6736(20) 30183-5

17 Kaempf, J. W., Wang, L., and Dunn, M. (2019). Using a composite morbidity score and cultural survey to explore characteristics of high proficiency neonatal intensive care units. Archives of Disease in 18 Childhood-Fetal and Neonatal Edition 104, F13-F17. doi:10.1136/archdischild-2017-313715

19 Korn, T., Mitsdoerffer, M., Croxford, A. L., Awasthi, A., Dardalhon, V. A., Galileos, G., et al. (2008). Il-6 controls th17 immunity in vivo by inhibiting the conversion of conventional t cells into foxp3+ regulator t cells. PNAS; Proceedings of the National Academy of Sciences 105, 18460-18465

20 Lane, T. R., Massey, C., Comer, J. E., Anantpadma, M., Freundlich, J. S., Davey, R. A., et al. (2019). Repurposing the antimalarial pyronaridine tetraphosphate to protect against ebola virus infection. PLOS 21 Neglected Tropical Diseases 13, 1-26. doi:10.1371/journal.pntd.0007890

22 Lee, D. W., Gardner, R., Porter, D. L., Louis, C. U., Ahmed, N., Jensen, M., et al. (2014). Current concepts in the diagnosis and management of cytokine release syndrome. Blood 124, 188-195. doi:10.1182/205 blood-2014-05-552729

23 Lescure, F.-X., Bouadma, L., Nguyen, D., Parisey, M., Wicky, P.-H., Behillil, S., et al. (2020), Clinical and virological data of the first cases of covid-19 in europe: a case series. *The Lancet Infectious Diseases*, doi:10.1016/s1473-3099(20)30200-0

24 Liu, B., Li, M., Zhou, Z., Guan, X., and Xiang, Y. (2020). Can we use interleukin-6 (il-6) blockade for coronavirus disease 2019 (covid-19)-induced cytokine release syndrome (crs)? Journal of Autoimmunity, 102452doi: 10.1016/j.jaut.2020.102452

25 Medesan, C., Cianga, P., Mummert, M., Stanescu, D., Ghetie, V., and Ward, E. S. (1998). Comparative studies of rat igg to further delineate the fc: for interaction site. European Journal of Immunology 28, 2092-2100. doi: 10.1002/(sici) 1521-4141(199807)28:07 2092::aid-immu2092 3.0.co;2-e 26 Mehta, P., McAuley, D. F., Brown, M., Sanchez, E., Tattersall, R. S., and Manson, J. J. (2020a). Covid-19: consider cytokine storm syndromes and immunosuppression. The Lancet 395, 1033-1034. doi:10.1016/s0140-6736(20)30628-0

27 Mehta, P., McAuley, D. F., Brown, M., Sanchez, E., Tattersall, R. S., and Manson, J. J. (2020b). Covid-19: consider cytokine storm syndromes and immunosuppression. The Lancet 395, 1033-1034. doi.org/10.1016/S0140-6736(20)30628-0

28 Ruan, Q., Yang, K., Wang, W., Jiang, L., and Song, J. (2020). Clinical predictors of mortality due to covid-19 based on an analysis of data of 150 patients from wuhan, china. *Intensive Care Medicine* 46, 846-848. doi:10.1007/s00134-020-05991-x 29 Rubsamen, R., Burkholz, S., Massey, C., Brasel, T., Hodge, T., Wang, L., Herst, C., Carback, R., and Harris, P. (2020). Anti-IL-6 Versus Anti-IL-6R Blocking Antibodies to Treat Acute Ebola Infection in BALB/c Mice: Potential Implications for treating cytokine Release Syndrome. Frontiers in Pharmacology, Vol. 11, Article 574703.

30 Saha, A., Sharma, A. R., Bhattacharya, M., Sharma, G., Lee, S.-S., and Chakraborty, C. (2020).

Tocilizumab: A therapeutic option for the treatment of cytokine storm syndrome in covid-19. Archives of Medical Research doi.org/10.1016/j.arcmed.2020.05.009

32 Sanofi (2017). Drug approval package: Kevzara (sarilumab) injection. U.S. Food & Drug Administration 33 Swaak, A. J., Rooyen, A. V., Nieuwenhuis, E., and Aarden, L. A. (1988). Interleukin-6 (il-6) in synovial fluid and serum of patients with rheumatic diseases. Scandinavian Journal of Rheumatology 17, 469-474. doi:10.3109/03009748809098809

34 Takamatsu, Y., Kolesnikova, L., and Becker, S. (2018). Ebola virus proteins np, vp35, and vp24 are essential and sufficient to mediate nucleocapsid transport. Proceedings of the National Academy of Sciences 115, 1075-1080 Tanaka, T., Narazaki, M., and Kishimoto, T. (2016). Immunotherapeutic implications of il-6 blockade for cytokine storm. Immunotherapy 8, 959-970. doi:10.2217/imt-2016-0020

35 Taylor, P. (2020). Novartis to test canakinumab for covid-19, as il-6 trial disappoints. PMLiVE 36 Vanoni, S., Tsai, Y.-T., Waddell, A., Waggoner, L., Klarquist, J., Divanovic, S., et al. (2017). Myeloid-derived nf-κβ negative regulation of pu. 1 and c/ebp-β-driven pro-inflammatory cytokine production restrains lps-induced shock. Innate Immunity 23, 175-187. doi: 10.1177/1753425916681444. PMID: 27932520

37 Wauquier, N., Becquart, C., Padilla, S., Baize, and E M, L. (2010). Human fatal zaire ebola virus infection is associated with an aberrant innate immunity and with massive lymphocyte apoptosis. Negl. Trop. Dis. 4. doi: 10.1371/journal.pntd.0000837

38 Wong, C. K., Lam, C. W. K., Wu, A. K. L., Ip, W. K., Lee, N. L. S., Chan, I. H. S., et al. (2004). Plasma inflammatory cytokines and chemokines in severe acute respiratory syndrome. Clinical & Experimental Immunology 136, 95-103. doi:10.1111/j.1365-2249.2004.02415.x 39 Xu, X., Han, M., Li, T., Sun, W., Wang, D., Fu, B., et al. (2020). Effective treatment of severe covid-19 patients with tocilizumab. PNAS; Proceedings of the National Academy of Sciences 117, 10970-10975

40 Zhou, F., Yu, T., Du, R., Fan, G., Liu, Y., Liu, Z., et al. (2020). Clinical course and risk factors for mortality of adult inpatients with covid-19 in wuhan, china: a retrospective cohort study.

41 The Lancet 251 395, 1054-1062. doi:10.1016/s0140-6736(20)30566-3

What is claimed is:

1. A method of treating, comprising:

diagnosing a patient with an infection of Ebola;

measuring a level of IL-6 in the patient to obtain an initial level;

administering to the patient by intramuscular injection a therapeutically effective amount of an injectable formulation of a therapeutically effective amount of siltuximab anti-IL-6 antibody encapsulated in a biocompatible polymer; and allowing the anti-IL-6 antibody to bind IL-6 cytokines in the patient and reduce cytokine release syndrome effects while allowing a level of free IL-6 cytokine to remain in the patient.

2. The method of claim 1, further comprising:

measuring a level of IL-6 in the patient after the administering step to obtain a post treatment level;

administering to the patient by intramuscular injection an additional amount of an injectable formulation of anti-IL-6 antibody encapsulated in a biocompatible polymer wherein the amount administered is based on a differential between the initial level and the post treatment level, and repeating the measuring and administering wherein the amount administered is in each administering step is based on a differential between a prior level and a subsequent post treatment level.

3. A method of treating, comprising:

diagnosing a patient with an Ebola infection;

administering to the patient at a first point in time a therapeutically effective amount of a first injectable formulation comprising a pharmaceutically acceptable carrier with free anti-IL-6 antibody, and allowing the free anti-IL-6 antibodies to bind IL-6 cytokines in the patient and provide for an initial phase of reducing cytokine release syndrome effects in the patient while leaving an amount of free IL-6 cytokines, and administering to the patient at a second point in time a therapeutically effective amount of a second injectable formulation comprising a pharmaceutically acceptable carrier with free anti-IL-6R antibody wherein the second point in time is at least one hour after the first point in time.

4. The method of claim 3, wherein the first injectable formulation further comprises free, unencapsulated IL-6 antibodies and IL-6 antibodies encapsulated in a biocompatible polymer, the second injectable formulation further comprises free, unencapsulated IL-6R antibodies and IL-6R antibodies encapsulated in a biocompatible polymer, and where the biocompatible polymer in the first and/or second injectable formulation releases antibodies producing an average plasma antibody level selected from the group consisting of (250 ug/ml, 200 ug/ml, 150 ug/ml, 100 ug/ml, 50 ug/ml)+/−5%, the method further comprising:

assaying cytokine blood levels in the patient;

re-administering the first or second injectable formulation to the patient based on determined cytokine levels, and wherein the biocompatible polymer of the first and/or second injectable formulation releases antibodies at an absorption rate which is characterized by an absorption rate constant (Ka (h−1)) selected from the group consisting of (0.001, 0.002, 0.004, 0.008, 0.016, 0.032, 0.064, 0.128, 0.256, 0.512, 1.024, 2.048)+/−5%.

5. A method of treating, comprising:

diagnosing a patient with an Ebola infection;

administering to the patient by injection at a first point in time a therapeutically effective amount of a first injectable formulation comprising a pharmaceutically acceptable carrier and free siltuximab, and allowing the free siltuximab to bind IL-6 cytokines in the patient and provide for an initial phase of reducing cytokine release syndrome effects in the patient while leaving a level of free IL-6 cytokines, and administering to the patient at a second point in time a therapeutically effective amount of a second injectable formulation comprising a pharmaceutically acceptable carrier with free anti-IL-6R antibody selected from the group consisting of sarilumab and tocilizumab, wherein the second point in time is at least one hour after the first point in time;

wherein the first and second injectable formulations are administered by a type of injection selected from the group consisting of subcutaneous and intramuscular and both formulations comprise free unencapsulated antibodies and antibodies encapsulated in a biocompatible polymer.

6. The method of claim 5, further comprising:

assaying cytokine blood levels in the patient; and re-administering at least one antibody formulation to the patient based on determined cytokine levels.

7. The method of claim 6, wherein the biocompatible polymer releases anti-IL-6R antibodies so as to produce an average plasma level selected from the group consisting of (250 ug/ml, 200 ug/ml, 150 μg/ml, 100 ug/ml, 50 ug/ml)+/−20%.

8. A method of treating, comprising:

diagnosing a patient with an Ebola infection;

administering to the patient by intravenous injection a therapeutically effective amount of an injectable formulation comprising a pharmaceutically acceptable carrier, and at least one anti-IL-6 antibody selected from siltuximab, wherein the formulation is injected at a rate so as to reduce cytokine release syndrome effects;

measuring the IL-6 cytokine blood level in the patient; and adjusting the dose and frequency of injection based on the measured cytokine level to allow for a level of IL-6 cytokines of about 5 to 7 μg/ml, thereby avoiding cytokine release syndrome while allowing for a level of circulating IL-6 cytokines.

* * * * *